US009206170B2

(12) United States Patent
Yang et al.

(10) Patent No.: US 9,206,170 B2
(45) Date of Patent: Dec. 8, 2015

(54) COMPOUND COMPRISING PHOSPHORESCENCE UNIT, EMITTING POLYMER AND ORGANIC EMITTING DEVICE COMPRISING THE EMITTING POLYMER

(75) Inventors: Hye-yeon Yang, Yongin-si (KR); Jhun-mo Son, Yongin-si (KR); Won-jae Joo, Yongin-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 382 days.

(21) Appl. No.: 12/435,480

(22) Filed: May 5, 2009

(65) Prior Publication Data

US 2010/0133992 A1  Jun. 3, 2010

(30) Foreign Application Priority Data

Nov. 28, 2008  (KR) ........................ 10-2008-0119939

(51) Int. Cl.
| | |
|---|---|
| H01L 51/54 | (2006.01) |
| C09K 11/06 | (2006.01) |
| C07D 413/14 | (2006.01) |
| C07D 265/38 | (2006.01) |
| C08G 61/12 | (2006.01) |
| H01L 51/00 | (2006.01) |
| H05B 33/14 | (2006.01) |
| C08K 5/00 | (2006.01) |
| C08K 5/56 | (2006.01) |
| H01L 51/50 | (2006.01) |

(52) U.S. Cl.
CPC ............ *C07D 413/14* (2013.01); *C07D 265/38* (2013.01); *C08G 61/122* (2013.01); *H01L 51/0039* (2013.01); *H01L 51/0043* (2013.01); *H01L 51/0085* (2013.01); *H05B 33/14* (2013.01); *C08G 2261/1526* (2013.01); *C08G 2261/344* (2013.01); *C08K 5/0091* (2013.01); *C08K 5/56* (2013.01); *C09K 2211/1416* (2013.01); *C09K 2211/1466* (2013.01); *C09K 2211/1475* (2013.01); *C09K 2211/185* (2013.01); *H01L 51/5016* (2013.01); *H01L 51/5036* (2013.01)

(58) Field of Classification Search
CPC ............... C08G 2261/1526; C08G 2261/3246; C08G 2261/344; C08G 61/122; H01L 51/0039; H01L 51/0043; H01L 51/5016; H01L 51/5036; H01L 51/0077–51/0092; C09K 11/06; C09K 2211/1475
See application file for complete search history.

(56) References Cited

U.S. PATENT DOCUMENTS

| | | | | |
|---|---|---|---|---|
| 6,630,254 B2 * | 10/2003 | Leclerc et al. | ................ | 428/690 |
| 6,979,414 B2 * | 12/2005 | Hosokawa | ............... | 252/301.16 |
| 2002/0045061 A1 | 4/2002 | Hosokawa | | |
| 2002/0173617 A1 * | 11/2002 | Yasuda et al. | ................. | 528/422 |
| 2004/0072989 A1 | 4/2004 | Son et al. | | |
| 2004/0135131 A1 * | 7/2004 | Treacher et al. | ............... | 252/582 |
| 2004/0137273 A1 * | 7/2004 | Tak et al. | ...................... | 428/690 |
| 2004/0260047 A1 * | 12/2004 | Chen et al. | ....................... | 528/4 |
| 2005/0186446 A1 * | 8/2005 | Shitagaki et al. | ............. | 428/690 |
| 2005/0244674 A1 * | 11/2005 | Yasuda et al. | ................. | 428/690 |
| 2007/0152573 A1 * | 7/2007 | Kim et al. | ..................... | 313/506 |

FOREIGN PATENT DOCUMENTS

| | | |
|---|---|---|
| CN | 1365381 A | 8/2002 |
| CN | 1366516 A | 8/2002 |
| CN | 1483783 A | 3/2004 |
| CN | 1534076 A | 10/2004 |
| CN | 1777592 A | 5/2006 |
| CN | 1974709 A | 6/2007 |
| EP | 1149827 A1 | 10/2001 |
| JP | 2005314505 A | 11/2005 |
| KR | 1020040059304 A | 7/2004 |
| KR | 1020080067931 A | 7/2008 |

OTHER PUBLICATIONS

Katsuhiko Ono, et al., "Synthesis and Electroluminescence Properties of fac-Tris(2-phenylpyridine)-iridium Derivatives Containing Hole-Trapping Moieties," European Journal of Inorganic Chemistry, 2006, pp. 3676-3683.
Japanese Patent Office Action dated Dec. 17, 2013 for related Application No. 2009-270107 with English translation, 5 pages.
Chinese Office Action for Chinese Patent Application No. 200910225874.6 dated Jan. 23, 2014 with English Translation.
Baldo et al., "Highly efficient phosphorescent emission from organic electroluminescent devices", Nature, vol. 395, Sep. 10, 1998, pp. 151-154.
Chinese Office Action for Chinese Patent Application No. 200910225874.6 issued May 6, 2013 with English Translation.
Chinese Office Action for Chinese Patent Application No. 200910225874.6 issued Jun. 19, 2014 with English Translation.

* cited by examiner

*Primary Examiner* — Michael H Wilson
(74) *Attorney, Agent, or Firm* — Cantor Colburn LLP

(57) ABSTRACT

Provided are compounds containing a phosphorescence unit, an emitting polymer, and an organic light emitting device (OLED) containing an organic layer including the emitting polymer. The OLED is useful in portable electronic equipment where low power consumption and low driving voltage are desirable.

6 Claims, 3 Drawing Sheets

COMPOUND COMPRISING PHOSPHORESCENCE UNIT, EMITTING POLYMER AND ORGANIC EMITTING DEVICE COMPRISING THE EMITTING POLYMER

CROSS-REFERENCE TO RELATED APPLICATIONS

This application claims priority to Korean Patent Application No. 10-2008-0119939, filed on Nov. 28, 2008, and all the benefits accruing therefrom under 35 U.S.C. §119, the contents of which in its entirety are incorporated herein by reference.

BACKGROUND

1. Field

One or more embodiments relate to a compound including a phosphorescence unit, an emitting polymer formed from the compound, and an organic light emitting device having an organic layer including the emitting polymer.

2. Description of the Related Art

Organic light emitting devices ("OLEDs"), which include a pair of electrodes and an organic layer interposed between the electrodes, are active light emitting display devices that emit light by recombination of electrons and holes injected through the electrodes in an organic layer when a current is applied to the organic layer through the electrodes. The OLEDs provide advantages such as lightweight, simple components, an easy fabrication process, excellent image quality, and wide viewing angles. In addition, the OLEDs can create perfect or near-perfect dynamic images and high color purity. The OLEDs also have electrical properties that are suitable for portable electronic equipment such as low power consumption and low driving voltage.

An OLED can have a structure formed as follows. An anode is formed on a substrate. A hole transport layer ("HTL"), an emitting layer ("EML"), and an electron transport layer ("ETL"), as organic layers, are sequentially formed on the anode. A cathode is formed thereon.

When a current is supplied to an anode and a cathode, holes injected from the anode are transported to the EML through the HTL, and electrons injected from the cathode are transported to the EML through the ETL. The transported holes and electrons are recombined in the EML to generate excitons. The radioactive decay of the excitons result in light emission, the light having a wavelength corresponding to a band gap of the molecule in the EML.

A material that is used to form an EML of an OLED can be classified as a fluorescent material using singlet excitons or a phosphorescent material using triplet excitons according to light emitting mechanisms. An EML can be formed using the fluorescent material or the phosphorescent material, or using a host material doped with the fluorescent material or the phosphorescent material. If the EML is formed using a host material, single excitons and triplet excitons are formed in the host material as a result of electron excitation. In this case, the singlet excitons and the triplet excitons are formed in a volume ratio of 1:3.

In an OLED using a fluorescent material for the formation of an EML, triplet excitons generated in a host are not used. However, in an OLED using a phosphorescent material for the formation of an EML, not only singlet excitons but also triplet excitons are used, thereby increasing internal quantum efficiency to 100%.

However, there is still a need to develop a high efficiency emitting material using phosphorescence that can be appropriately used for a high efficiency full color display or low power consumption white emitting device.

SUMMARY

One or more embodiments include a compound including a phosphorescence unit.

One or more embodiments include an emitting polymer.

One or more embodiments include an organic light emitting device ("OLED") having an organic layer including the emitting polymer.

Additional embodiments of the disclosure are described below.

One or more embodiments includes a compound represented by Formula 1 below:

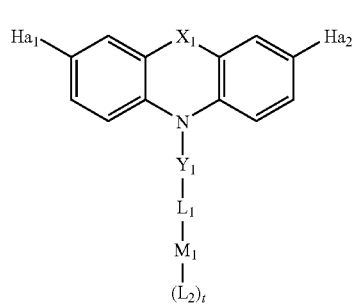

Formula 1 wherein $Ha_1$ and $Ha_2$ are each independently a halogen atom;

$X_1$ is O or S;

$Y_1$ is —$(CR_1R_2)_{n1}$— or —$(CR_3R_4)_{n2}$—O—, wherein $R_1$ to $R_4$ are each independently selected from a group consisting of a hydrogen atom, a hydroxyl group, an amino group, a cyano group, a carboxylic acid group, a $C_1$-$C_{20}$ alkyl group, and a $C_2$-$C_{20}$ alkenyl group, and n1 and n2 are each independently an integer of 0 to 20;

$M_1$ is a bivalent to tetravalent metal atom;

$L_1$ and $L_2$ are each independently an organic ligand represented by one of the Formulae 2, 3, 4 and 4a below, wherein if Formula 2 is $L_1$, one of the atoms in one of CY1 and CY2 of Formula 2 is connected to $Y_1$ via a single bond; if Formula 3 is $L_1$, one of the atoms in CY3 of Formula 3 is connected to $Y_1$ via a single bond; if Formula 4 is $L_1$, one of the atoms in CY4 of Formula 4 is connected to $Y_1$ via a single bond; and if Formula 4a is $L_1$, one of the atoms in $A_{10}$ is connected to $Y_1$ via a single bond;

t is 1 or 2,

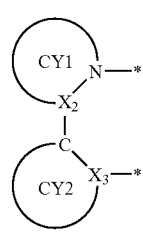

Formula 2

-continued

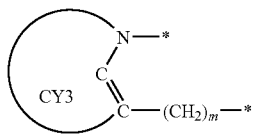

Formula 3

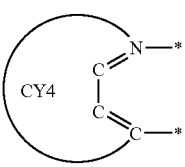

Formula 4

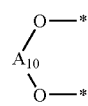

Formula 4a wherein $X_2$ and $X_3$ are each independently selected from the group consisting of C, S, O, and N;

CY1, CY3 and CY4 are each independently a substituted or unsubstituted heteroaromatic ring or a substituted or unsubstituted heteroaliphatic ring;

CY2 is selected from the group consisting of a substituted or unsubstituted aromatic ring, a substituted or unsubstituted heteroaromatic ring, a substituted or unsubstituted aliphatic ring, and a substituted or unsubstituted heteroaliphatic ring;

$A_{10}$ is $—(CR_{20}R_{21})_{n3}—$, wherein n3 is an integer of 1 to 10, at least one $—CR_{20}R_{21}—$ may be optionally replaced with $—NR_{22}—$, $—PR_{23}—$, or $—S—$, and $R_{20}$, $R_{21}$, $R_{22}$ and $R_{23}$ are each independently selected from the group consisting of a hydrogen atom, a hydroxyl group, an amino group, a cyano group, a carboxylic acid group, a $C_1$-$C_{20}$ alkyl group, and a $C_2$-$C_{20}$ alkenyl group;

m is an integer of 0 to 10; and

* is a binding site to $M_1$ of Formula 1.

To achieve the above and/or other aspects, one or more embodiments includes an emitting polymer represented by Formula 7 below:

$L_1$ and $L_2$ are each independently an organic ligand represented by one of the Formulae 2, 3, 4 and 4a, wherein if Formula 2 is $L_1$, one of the atoms in one of CY1 and CY2 of Formula 2 is connected to $Y_1$ via a single bond; if Formula 3 is $L_1$, one of the atoms in CY3 of Formula 3 is connected to $Y_1$ via a single bond; if Formula 4 is $L_1$, one of the atoms in CY4 of Formula 4 is connected to $Y_1$ via a single bond; and if Formula 4a is $L_1$, one of the atoms in $A_{10}$ of Formula 4a is connected to $Y_1$ via a single bond;

t is 1 or 2;

$X_4$ is O, S,

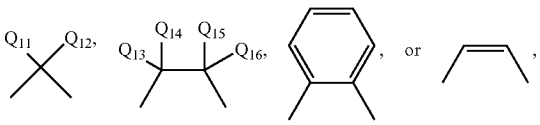

wherein $Q_{11}$, $Q_{12}$, $Q_{13}$, $Q_{14}$, $Q_{15}$ and $Q_{16}$ are each independently selected from a group consisting of a hydrogen atom, a $C_1$-$C_{20}$ alkyl group, and a $C_1$-$C_{20}$ alkoxy group;

$Y_2$ is a substituted or unsubstituted $C_6$-$C_{20}$ arylene group or a substituted or unsubstituted $C_4$-$C_{30}$ heteroarylene group;

R is selected from a group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_3$-$C_{30}$ cycloalkyl group, a substituted or unsubstituted $C_6$-$C_{30}$ aryl group, and a substituted or unsubstituted $C_6$-$C_{30}$ hetero aryl group; and a is a real number of $0<a\le 0.99$, b is a real number of $0\le a\le 0.99$, c is a real number of $0<c\le 0.99$, and d is a real number of $0\le d\le 0.99$, wherein a+b+c+d=1.

To achieve the above and/or other aspects, one or more embodiments include an OLED having an organic layer including the emitting polymer of Formula 7.

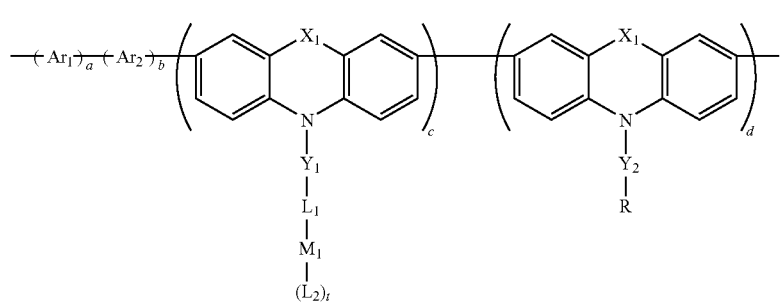

Formula 7 wherein $Ar_1$ and $Ar_2$ are each independently a substituted or unsubstituted $C_6$-$C_{30}$ arylene group or a substituted or unsubstituted $C_4$-$C_{30}$ heteroarylene group;

$X_1$ is O or S;

$Y_1$ is $—(CR_1R_2)_{n1}—$ or $—(CR_3R_4)_{n2}—O—$, wherein $R_1$ to $R_4$ are each independently selected from a group consisting of a hydrogen atom, a hydroxyl group, an amino group, a cyano group, a carboxylic acid group, a $C_1$-$C_{20}$ alkyl group, and a $C_2$-$C_{20}$ alkylene group, and n1 and n2 are each independently an integer of 0 to 20;

$M_1$ is a bivalent to tetravalent metal atom;

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
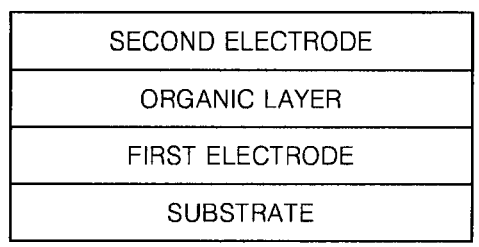
FIG. 1 is a schematic sectional view of an OLED according to an exemplary embodiment.

Reference will now be made in detail to embodiments, examples of which are illustrated in the drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present disclosure.

It will be understood that when an element or layer is referred to as being "on" or "connected to" another element or layer, the element or layer can be directly on or connected to another element or layer, or intervening elements or layers. In contrast, when an element is referred to as being "directly on" or "directly connected to" another element or layer, there are no intervening elements or layers present. Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, embodiments disclosed herein should not be construed as limited to the particular shapes of regions illustrated, but are to include deviations in shapes that result, for example, from manufacturing.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the exemplary embodiments of the invention.

As used herein, the singular forms "a," "an," and "the" are intended to include the plural embodiments as well, unless the context clearly indicates otherwise. As used herein, the term "and/or" includes any and all combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

For example, an implanted region illustrated as a rectangle will, typically, have rounded or curved features and/or a gradient of implant concentration at its edges rather than a binary change from implanted to non-implanted region. Likewise, a buried region formed by implantation can result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the embodiments as used herein.

A compound represented by Formula 1 below is provided.

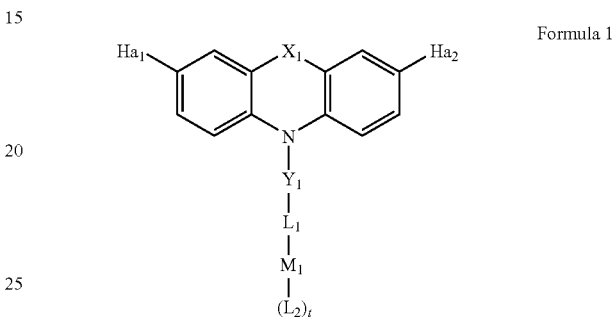

Formula 1

A compound represented by Formula 1 may be used as a monomer for the synthesis of a polymer represented by Formula 7, described below. The compound of Formula 1 includes a phosphorescence unit represented by $-L_1-M_1-(L_2)_t-$, which emits light based on a phosphorescence mechanism.

In Formula 1, $Ha_1$ and $Ha_2$ may be each independently a halogen atom. For example, $Ha_1$ and $Ha_2$ are each independently Cl, Br or I.

In Formula 1, $X_1$ may be O or S. For example, $X_1$ may be O, but is not limited thereto.

In Formula 1, $Y_1$ may be $-(CR_1R_2)_{n1}-$ or $-(CR_3R_4)_{n2}-O-$. Here, $R_1$ to $R_4$ may be each independently a hydrogen atom, a hydroxyl group, an amino group, a cyano group, a carboxylic acid group, a $C_1$-$C_{20}$ alkyl group or a $C_2$-$C_{20}$ alkenyl group, but is not limited thereto. For example, $R_1$ to $R_4$ may be each independently a hydrogen atom, a hydroxyl group, an amino group, a cyano group, a carboxylic acid group, a $C_1$-$C_{10}$ alkyl group, or a $C_2$-$C_{10}$ alkenyl group. In this regard, n1 and n2 may be each independently an integer of 0 to 20, for example, an integer of 0 to 10.

In Formula 1, $M_1$ may be a metal simultaneously having triplet and singlet states by a spin-orbital coupling arising from by a heavy atom effect. For example, $M_1$ may be a bivalent to tetravalent metal atom. $M_1$ may be Ir, Pt, Rh, Pd, Os, Ti, Zr, Hf, Eu, Tb, or Tm, but is not limited thereto.

In Formula 1, $L_1$ and $L_2$ may be each independently an organic ligand represented by one of Formulae 2, 3, 4 and 4a below.

Formula 2

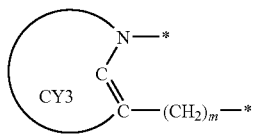

Formula 3

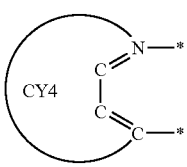

Formula 4

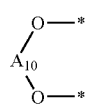

Formula 4a

In this regard, if Formula 2 is $L_1$, one of the atoms contained in one of CY1 and CY2 of Formula 2 is connected to $Y_1$ via a single bond. If Formula 3 is $L_1$, one of the atoms contained in CY3 of Formula 3 is connected to $Y_1$ via a single bond. If Formula 4 is $L_1$, one of the atoms contained in CY4 of Formula 4 is connected to $Y_1$ via a single bond. If Formula 4a is $L_1$, one of the atoms contained in $A_{10}$ is connected to $Y_1$ via a single bond. Formulae 5a to 5z below illustrate selected embodiments of the compound represented by Formula 1.1 In Formulae 2 to 4, $X_2$ and $X_3$ are each independently C, S, O, or N.

In Formulae 2 to 4, CY1, CY3 and CY4 are each independently a substituted or unsubstituted heteroaromatic ring or a substituted or unsubstituted heteroaliphatic ring, and CY2 is a substituted or unsubstituted aromatic ring, a substituted or unsubstituted heteroaromatic ring, a substituted or unsubstituted aliphatic ring, or a substituted or unsubstituted heteroaliphatic ring.

For example, the substituted or unsubstituted heteroaromatic ring may be selected from a group consisting of substituted or unsubstituted pyrrole, substituted or unsubstituted imidazole, substituted or unsubstituted pyrazole, substituted or unsubstituted pyridine, substituted or unsubstituted pyrazine, substituted or unsubstituted pyrimidine, substituted or unsubstituted pyridazine, substituted or unsubstituted isoindole, substituted or unsubstituted indole, substituted or unsubstituted indazole, substituted or unsubstituted purine, substituted or unsubstituted quinoline, substituted or unsubstituted benzoquinoline, substituted or unsubstituted phthalazine, substituted or unsubstituted naphthyridine, substituted or unsubstituted quinoxaline, substituted or unsubstituted quinazoline, substituted or unsubstituted cinnoline, substituted or unsubstituted carbazole, substituted or unsubstituted phenanthridine, substituted or unsubstituted acridine, substituted or unsubstituted phenanthroline, substituted or unsubstituted phenazine, substituted or unsubstituted benzooxazole, substituted or unsubstituted benzoimidazole, substituted or unsubstituted furan, substituted or unsubstituted benzofuran, substituted or unsubstituted thiophene, substituted or unsubstituted benzothiophene, substituted or unsubstituted thiazole, substituted or unsubstituted isothiazole, substituted or unsubstituted benzothiazole, substituted or unsubstituted isoxazole, substituted or unsubstituted oxazole, and substituted or unsubstituted benzooxazole, but is not limited thereto.

For example, the substituted or unsubstituted heteroaliphatic ring may be selected from a group consisting of substituted or unsubstituted pyrrolidine, substituted or unsubstituted pyrazolidine, substituted or unsubstituted imidazolidine, substituted or unsubstituted piperidine, substituted or unsubstituted piperazine, and substituted or unsubstituted morpholine, but is not limited thereto.

For example, the substituted or unsubstituted aromatic ring may be selected from a group consisting of substituted or unsubstituted benzene, substituted or unsubstituted pentalene, substituted or unsubstituted indene, substituted or unsubstituted naphthalene, substituted or unsubstituted azulene, substituted or unsubstituted heptalene, substituted or unsubstituted indacene, substituted or unsubstituted acenaphthylene, substituted or unsubstituted fluorine, substituted or unsubstituted phenalene, substituted or unsubstituted phenanthrene, substituted or unsubstituted anthracene, substituted or unsubstituted fluoranthene, substituted or unsubstituted triphenylene, substituted or unsubstituted pyrene, substituted or unsubstituted chrysene, substituted or unsubstituted naphthacene, substituted or unsubstituted picene, substituted or unsubstituted perylene, substituted or unsubstituted pentaphene, and substituted or unsubstituted hexacene, but is not limited thereto.

The substituted heteroaromatic ring, the substituted heteroaliphatic ring, the substituted aromatic ring, or the substituted aliphatic ring among the substituted or unsubstituted heteroaromatic ring, the substituted or unsubstituted heteroaliphatic ring, the substituted or unsubstituted aromatic ring, or the substituted or unsubstituted aliphatic ring may include at least one substituent selected from a group consisting of a halogen atom, —$CF_3$, —CN, —$Si(A_1)(A_2)(A_3)$, a $C_1$-$C_{20}$ alkyl group, a $C_2$-$C_{20}$ alkenyl group, a $C_6$-$C_{20}$ aryl group, a $C_1$-$C_{20}$ alkoxy group, a $C_6$-$C_{20}$ aryloxy group, and an amino group. In this regard, $A_1$, $A_2$ and $A_3$ may be each independently a hydrogen atom, a $C_1$-$C_{20}$ alkyl group, a $C_2$-$C_{20}$ alkenyl group, or a $C_1$-$C_{20}$ alkoxy group. The substituent may be a halogen atom, —$CF_3$, —CN, —$Si(A_1)(A_2)(A_3)$, a $C_1$-$C_{10}$ alkyl group, a $C_2$-$C_{10}$ alkenyl group, a $C_6$-$C_{14}$ aryl group, a $C_1$-$C_{10}$ alkoxy group, a $C_6$-$C_{14}$ aryloxy group, or an amino group, but is not limited thereto.

In Formulae 2 to 4, m may be an integer of 0 to 10. For example, m may be an integer of 0 to 5.

In Formulae 2 to 4, * is a binding site to $M_1$ of Formula 1.

In Formula 4a, $A_{10}$ may be represented by —$(CR_{20}R_{21})_{n3}$—. In this regard, n3 may be an integer of 1 to 10. For example, n3 may be an integer of 1 to 5, but is not limited thereto. At least one —$CR_{20}R_{21}$— may be optionally replaced with —$NR_{22}$—, —$PR_{23}$—, or —S—. The $R_{20}$, $R_{21}$, $R_{22}$ and $R_{23}$ are each independently a hydrogen atom, a hydroxyl group, an amino group, a cyano group, a carboxylic acid group, a $C_1$-$C_{20}$ alkyl group (for example, a methyl group, an ethyl group, a propyl group, and a butyl group) or a $C_2$-$C_{20}$ alkenyl group, but are not limited thereto.

In Formula 4a, * is a binding site to $M_1$ of Formula 1.

$L_1$ of Formula 1 may be represented by one of Formulae 5a to 5z, but is not limited thereto.

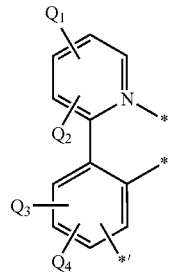

<Formula 5a>

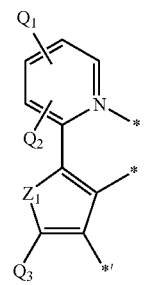
<Formula 5b>
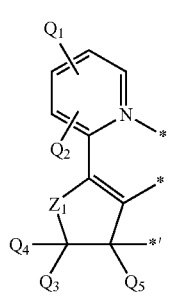
<Formula 5c>
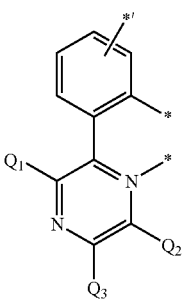
<Formula 5d>
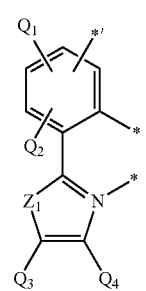
<Formula 5e>
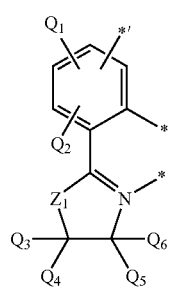
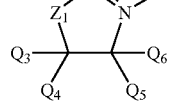
<Formula 5f>
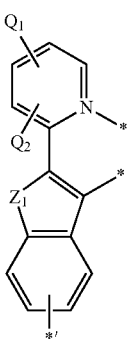
<Formula 5g>
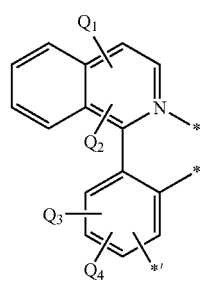
<Formula 5h>
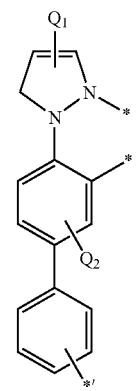
<Formula 5i>
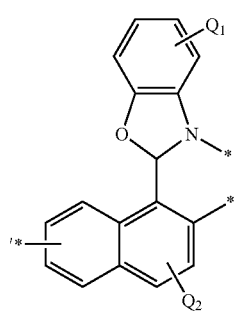
<Formula 5j>
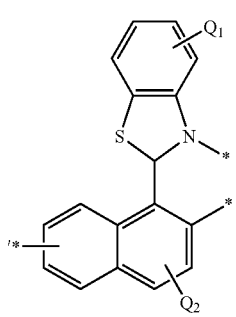
<Formula 5k>

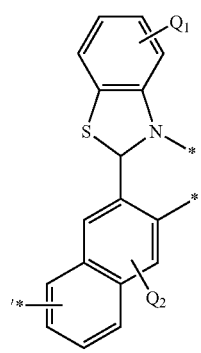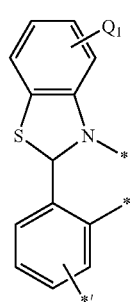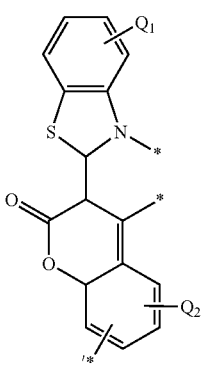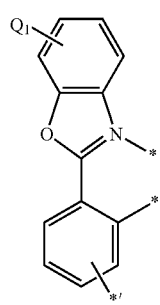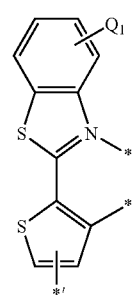
<Formula 5l>
<Formula 5m>
<Formula 5n>
<Formula 5o>
<Formula 5p>
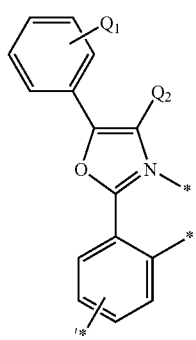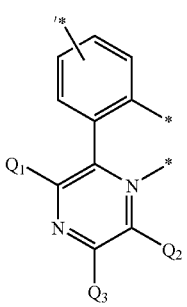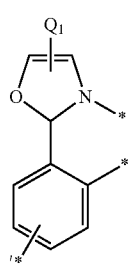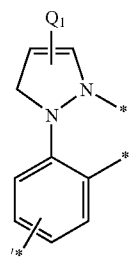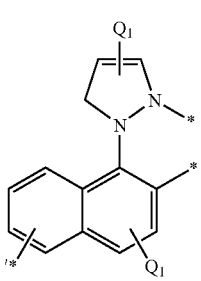
<Formula 5q>
<Formula 5r>
<Formula 5s>
<Formula 5t>
<Formula 5u>

-continued

<Formula 5v>
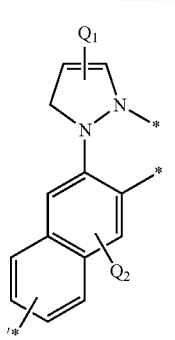

<Formula 5w>
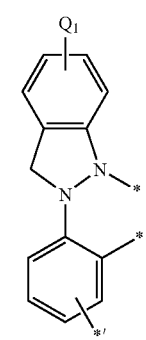

<Formula 5x>
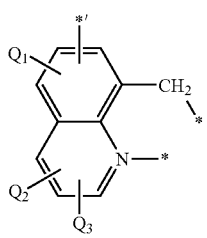

<Formula 5y>
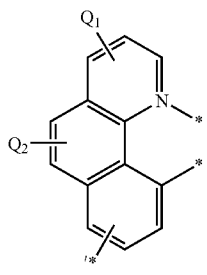

<Formula 5z>
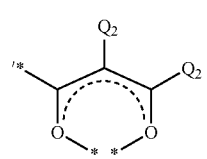

In Formulae 5a to 5z, $Z_1$ may be S, O, or N. In Formulae 5a to 5z, $Q_1, Q_2, Q_3, Q_4, Q_5, Q_6$ and $Q_7$ may be each independently a hydrogen atom, a halogen atom, —$CF_3$, —CN, —Si$(A_1)(A_2)(A_3)$, a $C_1$-$C_{20}$ alkyl group, a $C_2$-$C_{20}$ alkenyl group, a $C_6$-$C_{20}$ aryl group, a $C_1$-$C_{20}$ alkoxy group, a $C_6$-$C_{20}$ aryloxy group, or an amino group. For example, $Q_1, Q_2, Q_3, Q_4, Q_5, Q_6$ and $Q_7$ may be each independently a hydrogen atom, a halogen atom, —$CF_3$, —CN, —Si$(A_1)(A_2)(A_3)$, a $C_1$-$C_{10}$ alkyl group, a $C_2$-$C_{10}$ alkenyl group, a $C_6$-$C_{14}$ aryl group, a $C_1$-$C_{10}$ alkoxy group, a $C_6$-$C_{14}$ aryloxy group, or an amino group, but is not limited thereto.

At least two of $Q_1, Q_2, Q_3, Q_4, Q_5, Q_6,$ and $Q_7$ may be fused to form a 5-membered to 7-membered aliphatic or aromatic ring. Meanwhile, $A_1, A_2$ and $A_3$ are each independently a hydrogen atom, a $C_1$-$C_{20}$ alkyl group, a $C_2$-$C_{20}$ alkenyl group, or a $C_1$-$C_{20}$ alkoxy group, for example, a hydrogen atom, a $C_1$-$C_{10}$ alkyl group, a $C_2$-$C_{10}$ alkenyl group, or a $C_1$-$C_{10}$ alkoxy group, but are not limited thereto.

In Formulae 5a to 5z, *' is a binding site to $Y_1$ of Formula 1.

In Formulae 5a to 5z, * is a binding site to $M_1$ of Formula 1.

In Formula 1, $L_2$ may be represented by one of Formula 6a to 6z, but is not limited thereto.

<Formula 6a>
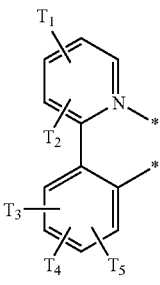

<Formula 6b>
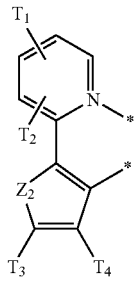

<Formula 6c>
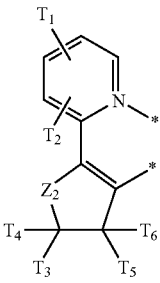

<Formula 6d>
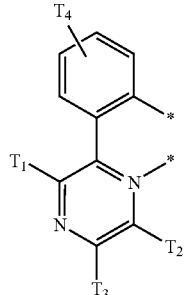

<Formula 6e>
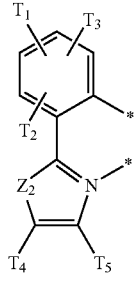

<Formula 6f>
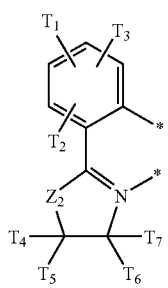
<Formula 6g>
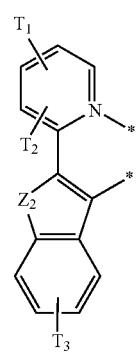
<Formula 6h>
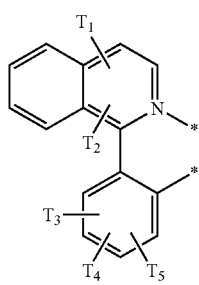
<Formula 6i>
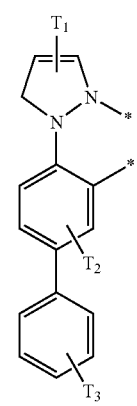
<Formula 6j>
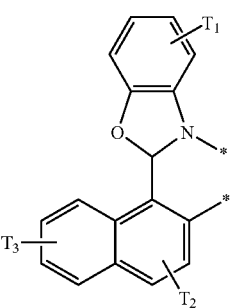
<Formula 6k>
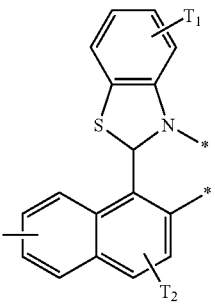
<Formula 6l>
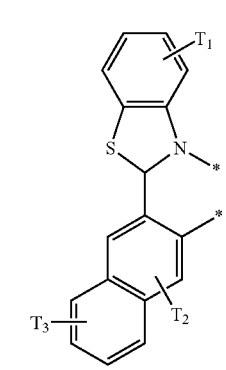
<Formula 6m>
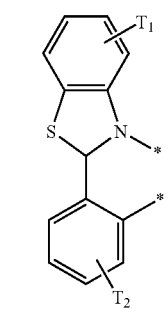
<Formula 6n>
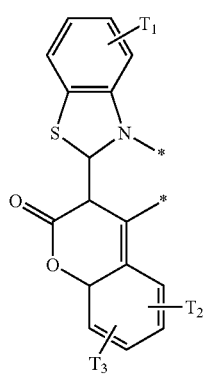
<Formula 6o>
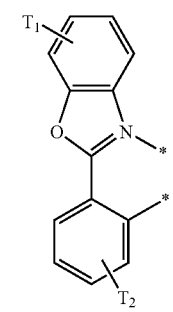

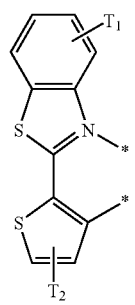
<Formula 6p>
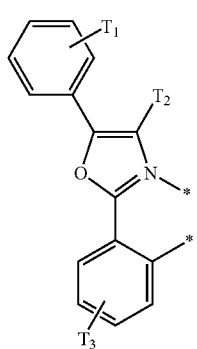
<Formula 6q>
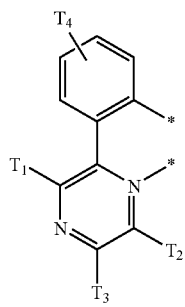
<Formula 6r>
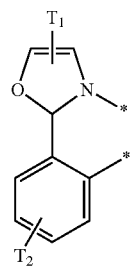
<Formula 6s>
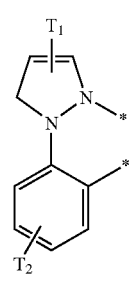
<Formula 6t>
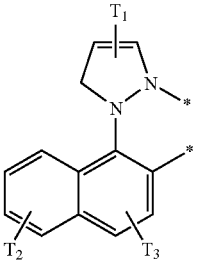
<Formula 6u>
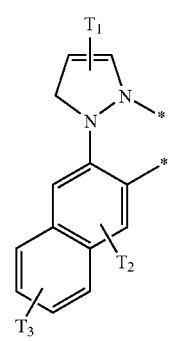
<Formula 6v>
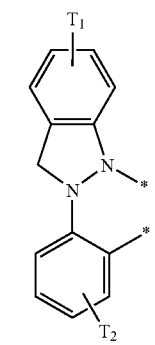
<Formula 6w>
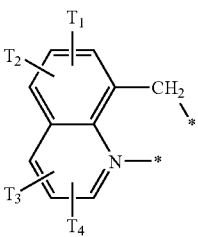
<Formula 6x>
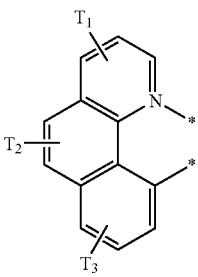
<Formula 6y>
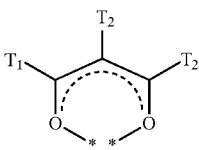
<Formula 6z>

In Formulae 6a to 6z, $Z_2$ is S, O, or N.

In Formulae 6a to 6z, $T_1$, $T_2$, $T_3$, $T_4$, $T_5$, $T_6$, $T_7$ and $T_8$ are each independently a hydrogen atom, a halogen atom, —$CF_3$, —CN, —$Si(A_4)(A_5)(A_6)$, a $C_1$-$C_{20}$ alkyl group, a $C_2$-$C_{20}$ alkenyl group, a $C_6$-$C_{20}$ aryl group, a $C_1$-$C_{20}$ alkoxy group, a $C_6$-$C_{20}$ aryloxy group, or an amino group. For example, $T_2$, $T_3$, $T_4$, $T_5$, $T_6$, $T_7$ and $T_8$ may be each independently a hydrogen atom, a halogen atom, —$CF_3$, —CN, —$Si(A_4)(A_5)(A_6)$, a $C_1$-$C_{10}$ alkyl group, a $C_2$-$C_{10}$ alkenyl group, a $C_6$-$C_{10}$ aryl group, a $C_1$-$C_{10}$ alkoxy group, a $C_6$-$C_{10}$ aryloxy group, or an amino group.

At least two of $T_1$, $T_2$, $T_3$, $T_4$, $T_5$, $T_6$, $T_7$, and $T_8$ may be fused to form a 5-membered to 7-membered aliphatic or aromatic ring. Meanwhile, $A_4$, $A_5$ and $A_6$ are each independently, a hydrogen atom, a $C_1$-$C_{20}$ alkyl group, a $C_2$-$C_{20}$ alkenyl group, or a $C_1$-$C_{20}$ alkoxy group, for example, a hydrogen atom, a $C_1$-$C_{12}$ alkyl group, a $C_2$-$C_{12}$ alkenyl group, or a $C_1$-$C_{12}$ alkoxy group.

In Formulae 6a to 6z, * is a binding site to $M_1$ of Formula 1.

The compound of Formula 1 may be Compound 1, 2, or 3, but is not limited thereto.

Compound 1

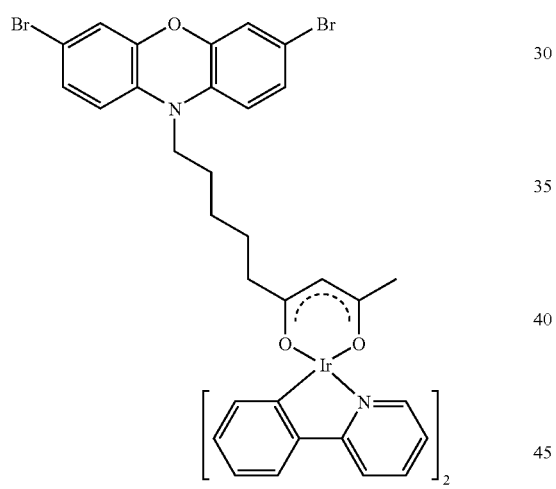

Compound 2

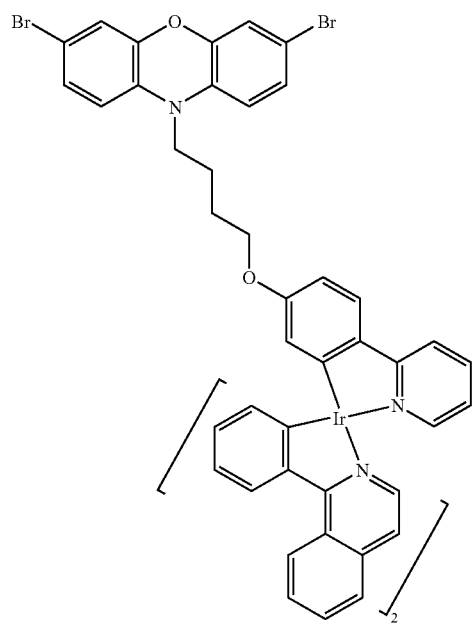

Compound 3

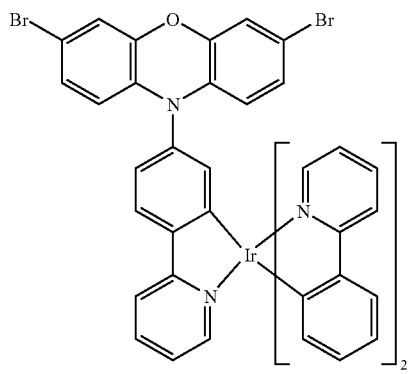

According to another embodiment, a polymer represented by Formula 7 is provided.

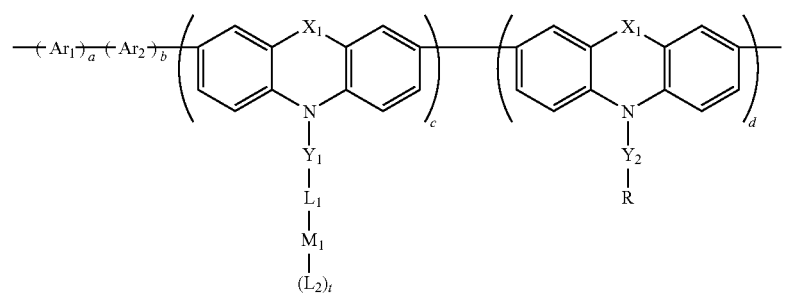

Formula 7

The polymer of Formula 7 may emit one or at least two colored lights based on a phosphorescence mechanism and/or a fluorescence mechanism. By using the polymer, a high quality organic light emitting device (OLED) may be manufactured.

The polymer of Formula 7 may emit light in a repeating unit represented by Formula U1

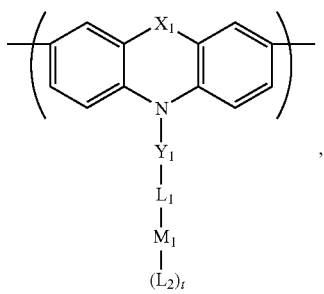

Formula U1 based on a phosphorescence mechanism, or in a repeating unit represented by —(Ar$_1$)—, —(Ar$_2$)—, and/or a unit represented by Formula U2

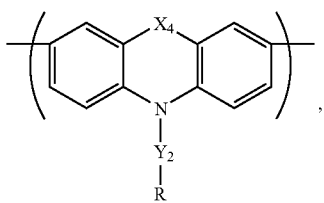

Formula U2 based on a fluorescence mechanism. Thus, high internal quantum efficiency may be obtained. Since the phosphorescence unit of -(L$_1$)-M$_1$-(L$_2$)$_t$- is combined with a phenoxazine moiety or phenothiazine moiety in the polymer of Formula 7, electroluminescence properties may be observed not only in a backbone of the polymer of Formula 7 but also in the phosphorescence unit. In addition, intermolecular energy transfer may occur in the polymer, thereby providing excellent efficiency.

The polymer of Formula 7 may simultaneously emit at least two colored lights. For example, the polymer of Formula 7 may emit red light and/or green light in a repeating unit represented by Formula U3

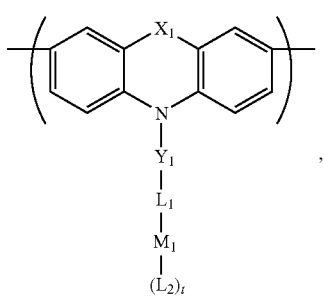

Formula U3 and blue light in a repeating unit represented by —(Ar$_1$)—, —(Ar$_2$)—, and/or Formula U4

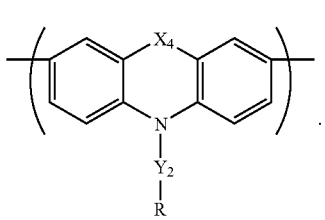

Formula U4

Accordingly, a variety of colors may be combined according to the structure and molar ratio of the repeating units. For example, the polymer of Formula 7 may emit white light.

In Formula 7, Ar$_1$ and Ar$_2$ may be each independently a substituted or unsubstituted C$_6$-C$_{30}$ arylene group or a substituted or unsubstituted C$_4$-C$_{30}$ heteroarylene group.

A$_1$ and Ar$_2$ may be represented by one of Formulae 8a to 8s below, but are not limited thereto.

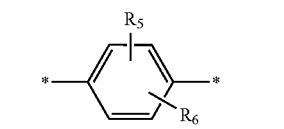

<Formula 8a>

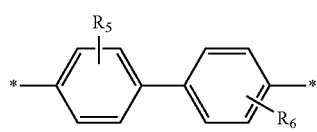

<Formula 8b>

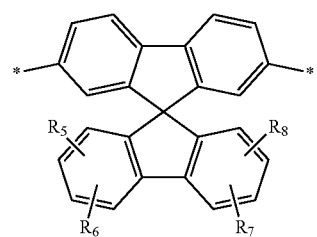

<Formula 8c>

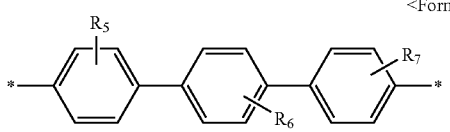

<Formula 8d>

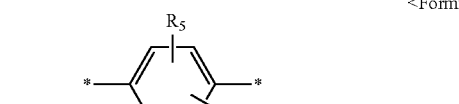

<Formula 8e>

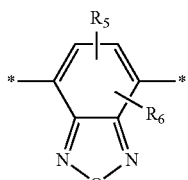

<Formula 8f>

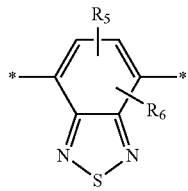

<Formula 8g>

<Formula 8h>

<Formula 8i>

<Formula 8j>

<Formula 8k>

<Formula 8l>

<Formula 8m>

<Formula 8n>

<Formula 8o>

<Formula 8p>

<Formula 8q>

<Formula 8r>

<Formula 8s>

In Formulae 8a to 8s, $R_5$ to $R_8$ may be each independently a hydrogen atom, $C_1$-$C_{20}$ alkyl group, a $C_1$-$C_{20}$ alkoxy group, or a $C_6$-$C_{20}$ aryl group. For example, $R_5$ to $R_8$ may be each independently a hydrogen atom, a $C_1$-$C_{10}$ alkyl group, a $C_1$-$C_{10}$ alkoxy group, or a $C_6$-$C_{10}$ aryl group.

In Formulae 8a to 8s, * is a binding site to an adjacent repeating unit.

In Formula 7, $X_1$, $Y_1$, $M_1$, $L_1$, $L_2$ and t are described above with reference to Formula 1.

In Formula 7, $X_4$ may be O, S,

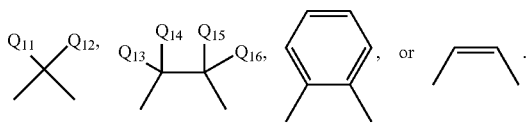

For example, $X_4$ may be O or S. $Q_{11}$, $Q_{12}$, $Q_{13}$, $Q_{14}$, $Q_{15}$ and $Q_{16}$ may be each independently a hydrogen atom, a $C_1$-$C_{20}$ alkyl group, or a $C_1$-$C_{20}$ alkoxy group. For example, $Q_{11}$, $Q_{12}$, $Q_{13}$, $Q_{14}$, $Q_{15}$ and $Q_{16}$ may be each independently a hydrogen atom, a $C_1$-$C_{10}$ alkyl group, or a $C_1$-$C_{10}$ alkoxy group.

In Formula 7, $Y_2$ may be a substituted or unsubstituted $C_6$-$C_{30}$ arylene group or a substituted or unsubstituted $C_4$-$C_{30}$ heteroarylene group. For example, $Y_2$ may be a substituted or unsubstituted $C_6$-$C_{14}$ arylene group. $Y_2$ may be a phenylene group, a naphthylene group, or an anthrylene group. The substituent of the substituted arylene group and heteroarylene group may be a cyano group, a hydroxy group, a thiol group, a nitro group, a halogen atom, a $C_1$-$C_{10}$ alkyl group, a $C_1$-$C_{10}$ alkoxy group, a $C_2$-$C_{10}$ alkenyl group, or a $C_6$-$C_{14}$ aryl group, but is not limited thereto.

In Formula 7, R may be a hydrogen atom, a substituted or unsubstituted $C_1$-$C_{20}$ alkyl group (for example, a $C_1$-$C_{12}$ alkyl group), a substituted or unsubstituted $C_1$-$C_{20}$ alkoxy group (for example, a $C_1$-$C_{12}$ alkoxy group), a substituted or unsubstituted $C_3$-$C_{30}$ cycloalkyl group (for example, a $C_3$-$C_{12}$ cycloalkyl group), a substituted or unsubstituted $C_6$-$C_{30}$ aryl group (for example, a $C_6$-$C_{14}$ aryl group) or a substituted or unsubstituted $C_6$-$C_{30}$ hetero aryl group (for example, a $C_6$-$C_{14}$ hetero aryl group). In this regard, at least one hydrogen atom of the aryl group or hetero aryl group may be unsubstituted or substituted with a $C_1$-$C_{12}$ alkyl group, a $C_1$-$C_{12}$ alkoxy group, or —N($Z_1$)($Z_2$), wherein $Z_1$ and $Z_2$ are each independently a hydrogen atom or a $C_1$-$C_{12}$ alkyl group.

In Formula 7, a may be a real number of $0<a\leq0.99$, b may be a real number of $0\leq b\leq0.99$, c may be a real number of $0<c\leq0.99$, and d may be a real number of $0\leq d\leq0.99$, wherein a+b+c+d=1. That is, b and/or d may be 0, a and c may not be 0. For example, a may be a real number of $0.5<a\leq0.95$, b may be a real number of $0\leq b\leq0.95$, c may be a real number of $0.5<c\leq0.95$, and d may be a real number of $0\leq d\leq0.95$, wherein a+b+c+d=1.

The polymer of Formula 7 may have a weight average molecular weight of about 10,000 to about 500,000, for example, about 200,000 to about 400,000. If the polymer of Formula 7 has a weight average molecular weight described above, the polymer may be used in an organic layer of an OLED providing excellent lifetime, high brightness, etc.

A molecular weight distribution (i.e., the polydispersity index ("PDI")) of the polymer of Formula 7 may be from about 1.5 to about 5, for example about 2 to about 3. If the polymer of Formula 7 has a molecular weight distribution (polydispersity) described above, the polymer may be used in an organic layer of an OLED providing excellent lifetime, high brightness, etc.

The polymer of Formula 7 may be represented by one of Formulae 7a to 7d below, but is not limited thereto.

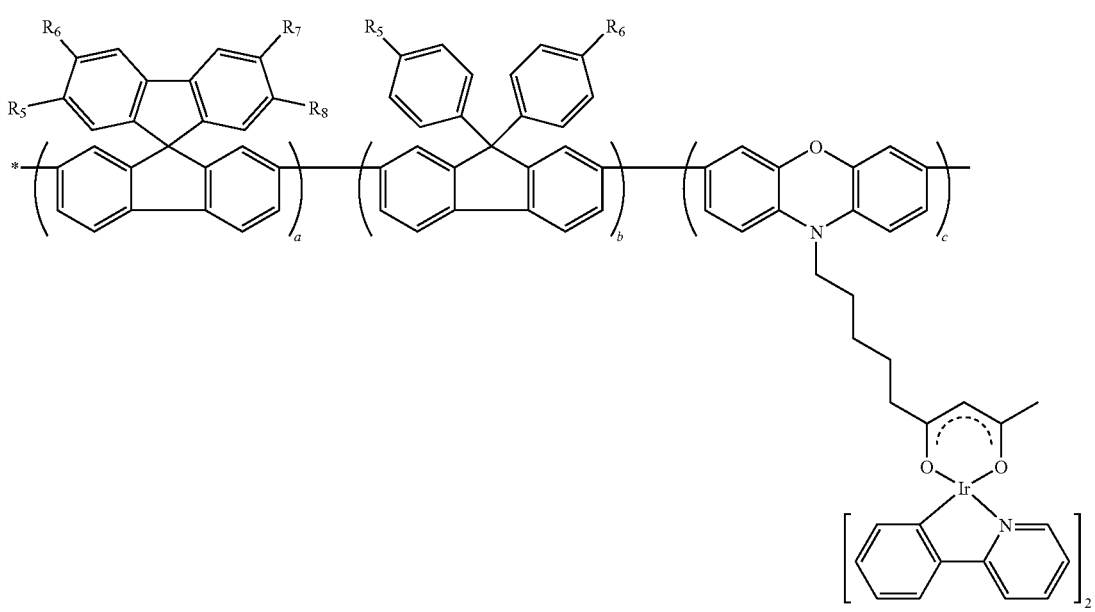

Formula 7a

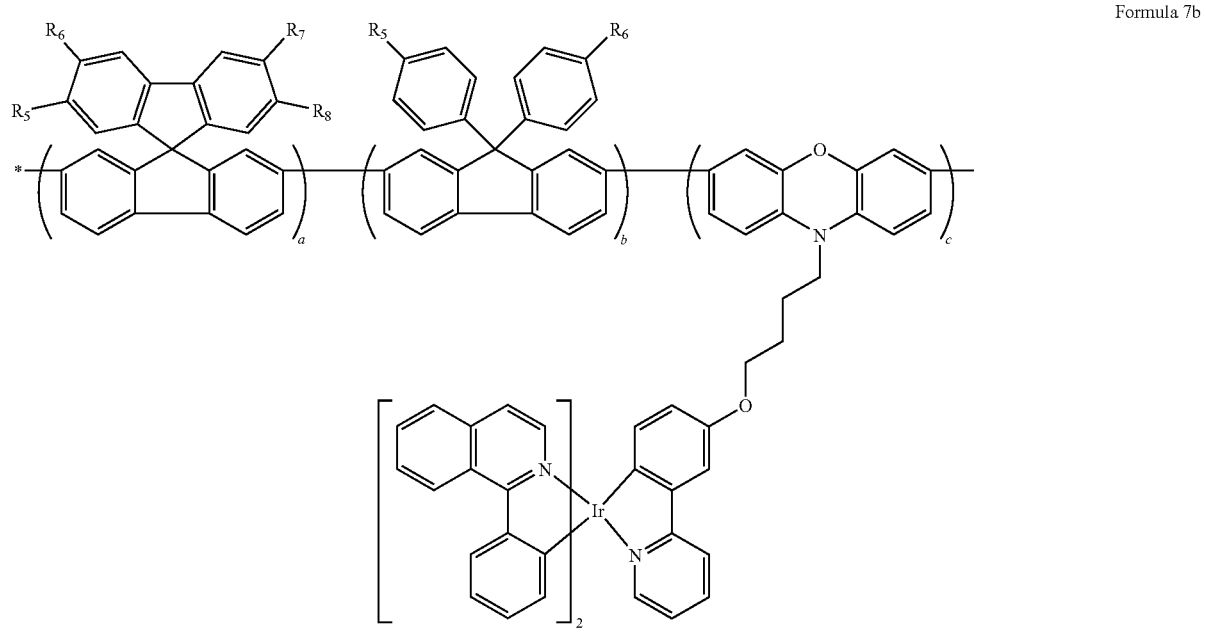
Formula 7b
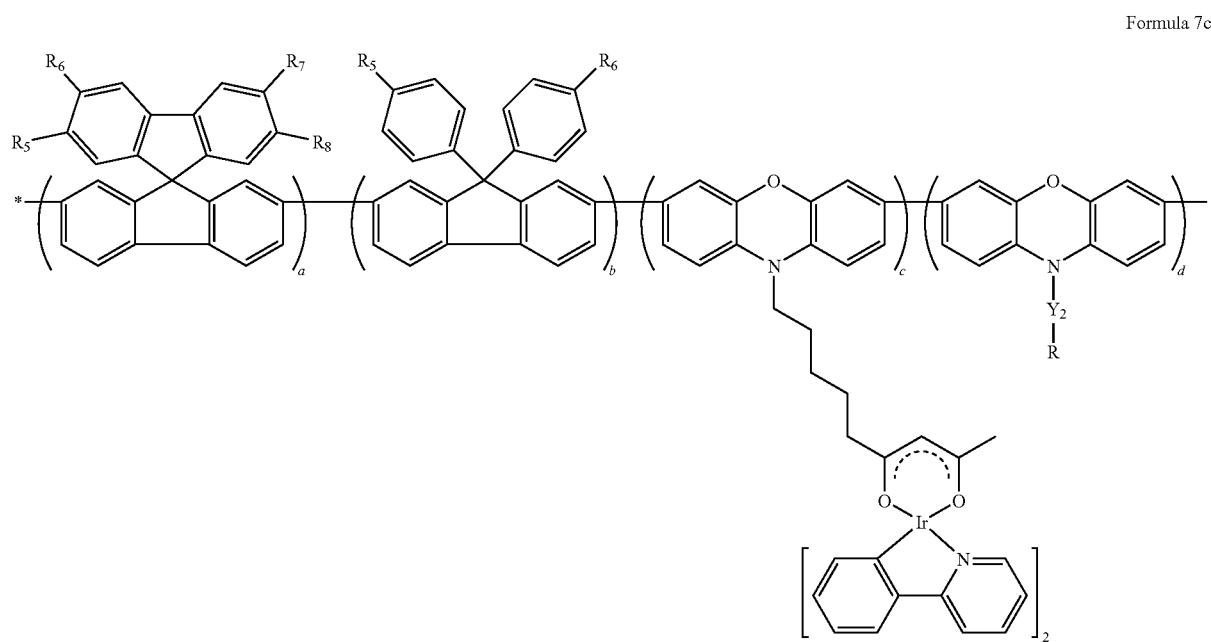
Formula 7c

Formula 7d

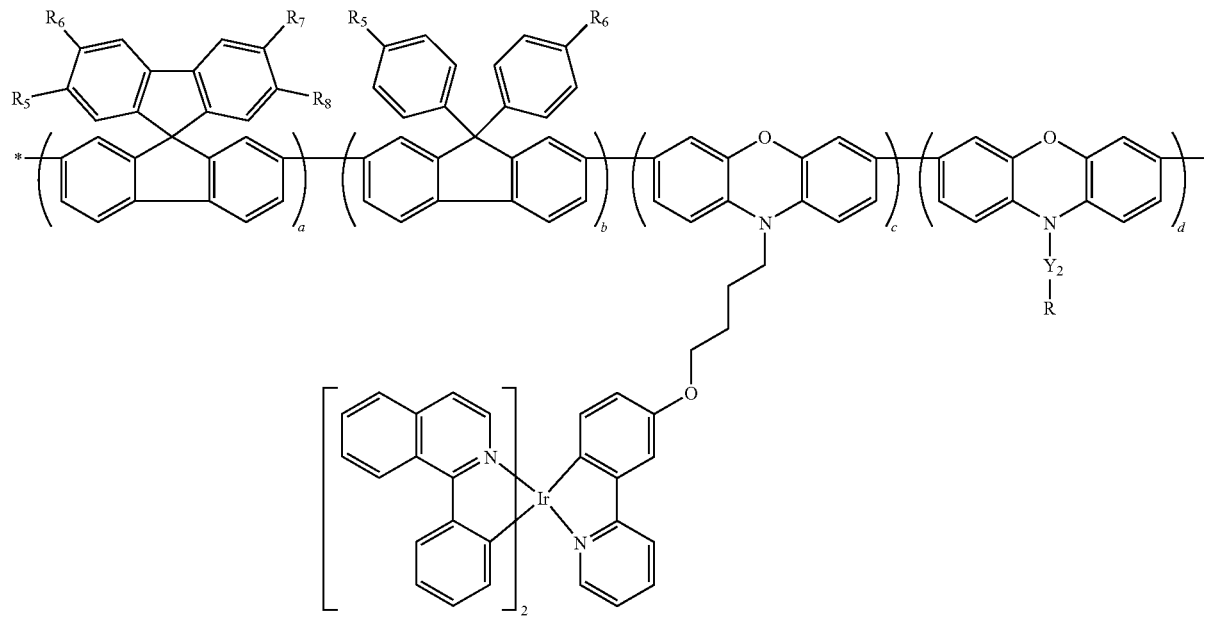

In Formulae 7a to 7d, $R_5$ to $R_8$ may be each independently a hydrogen atom, a $C_1$-$C_{20}$ alkyl group, a $C_1$-$C_{20}$ alkoxy group, or a $C_6$-$C_{30}$ aryl group, a is a real number of $0<a\leq0.99$, b is a real number of $0\leq b\leq0.99$, c is a real number of $0<c\leq0.99$, and d is a real number of $0\leq d\leq0.99$, wherein a+b+c+d=1.

In Formulae 7c and 7d, $Y_2$ and R are described above.

The unsubstituted $C_1$-$C_{20}$ alkyl group may be a methyl group, an ethyl group, a propyl group, an isobutyl group, a sec-butyl, a pentyl group, an iso-amyl group, and a hexyl group. At least one hydrogen atom of the alkyl group may be substituted with a substituent such as a halogen atom, a $C_1$-$C_{30}$ alkyl group, a $C_1$-$C_{30}$ alkoxy group, a low alkylamino group, a hydroxy group, a nitro group, a cyano group, an amino group, an amidino group, hydrazine, hydrazone, a carboxyl group, a sulfonyl group, and a phosphate group.

The unsubstituted $C_2$-$C_{20}$ alkenyl group may be an ethenyl group. At least one hydrogen atom of the alkenyl group may be substituted with the substituent described above with reference to the $C_1$-$C_{20}$ alkyl group.

The unsubstituted $C_1$-$C_{20}$ alkoxy group may be a methoxy group, an ethoxy group, a propoxy group, an isobutyloxy group, a sec-butyloxy group, a pentyloxy group, an iso-amyloxy group, and a hexyloxy group. At least one hydrogen atom of the alkoxy group may be substituted with the substituent described above with reference to the $C_1$-$C_{20}$ alkyl group.

The $C_6$-$C_{30}$ aryl group indicates a carbocyclic aromatic system containing one or more rings, wherein such rings may be bonded together in a pendent manner or may be fused. The term "aryl group" may include an aromatic system such as a phenyl group, a naphthyl group, and a tetrahydronaphthyl group. At least one hydrogen atom in the aryl group may be substituted with the substituent described above with reference to the $C_1$-$C_{20}$ alkyl group.

The $C_4$-$C_{30}$ hetero aryl group indicates a monovalent monocyclic ring compound having 2 to 30 membered rings including C and 1 to 3 hetero atoms selected from the group consisting of N, O, P, and S, wherein such rings may be bonded together in a pendent manner or may be fused. Examples of the heteroaryl group may include a pyridyl group, a thienyl group, and a furyl group. At least one hydrogen atom in the heteroaryl group may be substituted with the substituent described above with reference to the $C_1$-$C_{20}$ alkyl group.

The $C_5$-$C_{30}$ cycloalkyl group is a cyclic alkyl group, for example a cyclohexyl group, and at least one hydrogen atom in the cycloalkyl group may be substituted with the substituent described above with reference to the $C_1$-$C_{20}$ alkyl group.

The $C_5$-$C_{30}$ cycloalkyl group is a cyclic alkyl group, for example a cyclohexyl group, and at least one hydrogen atom in the cycloalkyl group can be substituted with the substituent described above with reference to the $C_1$-$C_{20}$ alkyl group.

The $C_5$-$C_{30}$ heterocycloalkyl group is a group in which at least one of C of the cycloalkyl group is substituted with at least one hetero atoms selected from the group consisting of N, O, P and S, and can be a pyrrolidinyl group and an imidazolidinyl group. At least one hydrogen atom in the heterocycloalkyl group can be substituted with the substituent described above with reference to the $C_1$-$C_{20}$ alkyl group.

The polymer of Formula 7 may be synthesized using a well-known polymer synthesis method such as Suzuki coupling or Yamamoto coupling.

For example, the polymer of Formula 7 may be synthesized by synthesizing a compound represented by Formula 9, and binding -$M_1$-$(L_2)_t$ to a terminal of $L_1$ of the compound of Formula 9.

Formula 9

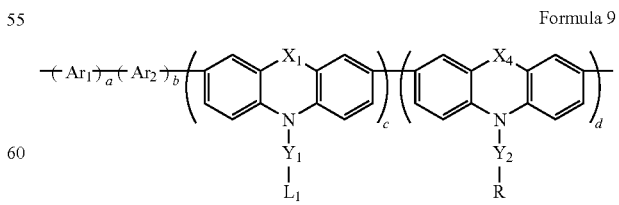

In Formula 9, $Ar_1$, $Ar_2$, $X_1$, $Y_1$, $L_1$, $X_4$, $Y_2$, R, and a to d are described above.

Alternatively, the polymer of Formula 7 may be synthesized by Suzuki coupling using a compound represented by Formula 1, as a comonomer, and a monomer providing —(Ar₁)— repeating unit, —(Ar₂)— repeating unit and/or a repeating unit of formula U2:

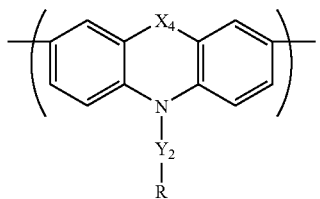

Formula U2

If the polymer of Formula 7 is synthesized using the compound of Formula 1, the binding site and binding molar ratio of a phosphorescence unit of -L$_1$-M$_1$-(L$_2$)$_t$ in Formula 7 may be easily controlled.

According to another embodiment, an OLED including an organic layer including a polymer represented by Formula 7 is provided. The OLED may include a pair of electrodes and an organic layer interposed between the electrodes, wherein the organic layer may include the polymer represented by Formula 7. The organic layer including the emitting polymer may be an emitting layer ("EML").

The polymer of Formula 7 may be used alone or used with a known host material. Examples of the host material are Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), and 3-tert-butyl-9,10-di-2-naphthylanthracene (TBADN), but are not limited thereto.

If the polymer of Formula 7 is used with a host material, the concentration of the host material may be in a range of about 10 to about 30 parts by weight based on 100 parts by weight of the polymer, but is not limited.

The OLED containing the organic layer including the emitting polymer may have excellent lifetime, brightness, efficiency, color purity, and the like. Furthermore, white emitting may be realized by combining colored lights since the emitting polymer may emit at least two colored lights.

FIG. 1 is a schematic sectional view of an OLED according to an embodiment. Referring to FIG. 1, the OLED includes a substrate, a first electrode, an EML including a polymer represented by Formula 7, and a second electrode. A method of manufacturing an OLED according to an embodiment is described below with reference to the OLED illustrated in FIG. 1.

First, a first electrode is formed by depositing or sputtering a high work-function material on a substrate. The first electrode can be an anode. The substrate, which can be any substrate that is used in organic light emitting devices, may be a glass substrate or a transparent plastic substrate that has excellent mechanical strength, thermal stability, transparency, and surface smoothness, is easily treated, and is waterproof. The first electrode may be formed of ITO, IZO, SnO$_2$, ZnO, or any transparent material that has high conductivity.

Then, at least one of a hole injection layer ("HIL") and a hole transport layer ("HTL") may be formed on the first electrode, if desired, even though not shown in FIG. 1.

The HIL may be formed by vacuum deposition, spin coating, casting, Langmuir Blodgett ("LB"), or the like.

When the HIL is formed by vacuum deposition, vacuum deposition conditions may vary according to the compound that is used to form the HIL, and the desired structure and thermal properties of the HIL to be formed. In general, however, the vacuum deposition may be performed at a deposition temperature of about 100 to about 500° C., under a pressure of about 10$^{-8}$ to about 10$^{-3}$ torr, and at a deposition speed of about 0.01 to about 100 Å/sec.

When the HIL is formed by spin coating, coating conditions may vary according to a compound that is used to form the HIL, and the desired structure and thermal properties of the HIL to be formed. In general, however, the coating speed may be in a range of about 2000 to about 5000 rpm, and a temperature for heat treatment, which is performed to remove a solvent after coating, may be in a range of about 80 to about 200° C.

The HIL may be formed of a known material. The material may be, for example, a phthalocyanine compound, such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), or the like, but is not limited thereto.

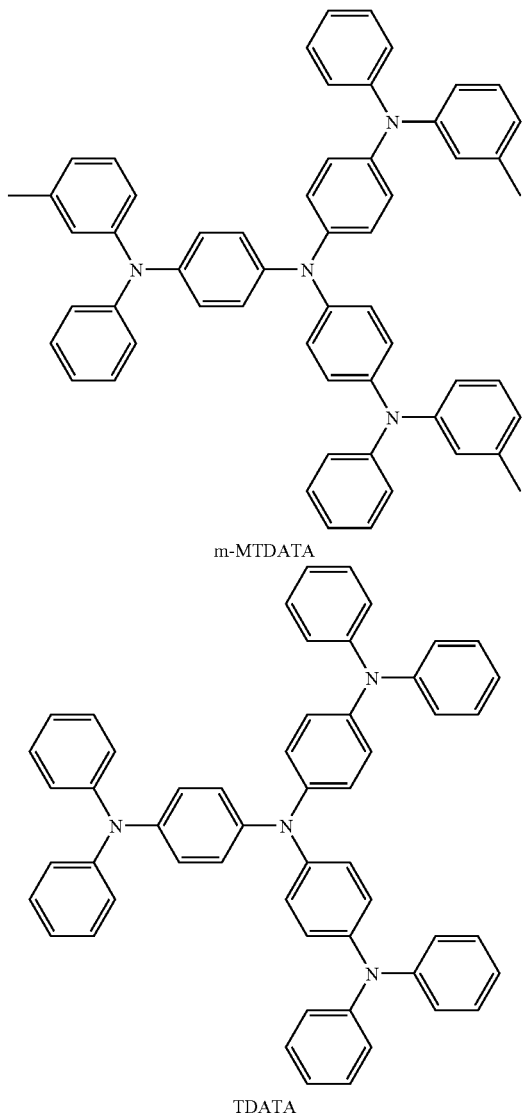

m-MTDATA

TDATA

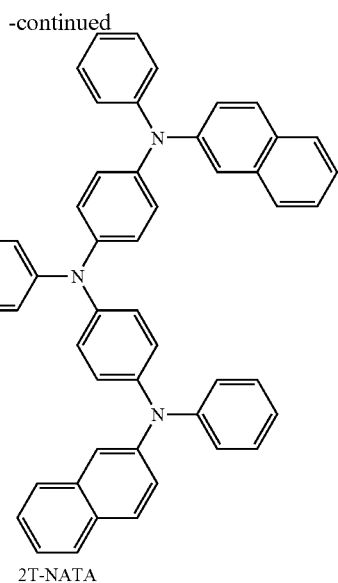

2T-NATA

The thickness of the HIL may be in a range of about 100 to about 10000 Å, for example, in a range of about 100 to about 1000 Å. When the thickness of the HIL is less than about 100 Å, the hole injecting ability of the HIL may be reduced. On the other hand, when the thickness of the HIL is greater than about 10000 Å, the driving voltage of the device may be increased.

Then, a hole transport layer ("HTL") may be formed on the HIL using vacuum deposition, spin coating, casting, LB, or the like. When the HTL is formed by vacuum deposition or spin coating, the conditions for deposition and coating are similar to those for the formation of the HIL, although conditions for the deposition and coating may vary according to the material that is used to form the HTL.

The HTL may be formed of a known material. The material may be, for example, a carbazole derivative, such as N-phenylcarbazole and polyvinylcarbazole; an amine derivative having an aromatic condensation ring such as N,N'-bis(3-methylphenyl)-N,N'-diphenyl-[1,1-biphenyl]-4,4'-diamine (TPD) and N,N'-di(naphthalene-1-yl)-N,N'-diphenyl benzydine (α-NPD); or triphenylamine such as 4,4',4''-tris(N-carbazolyl)triphenylamine (TCTA). The TCTA may also inhibit excitons from being diffused from the EML in addition to transport holes.

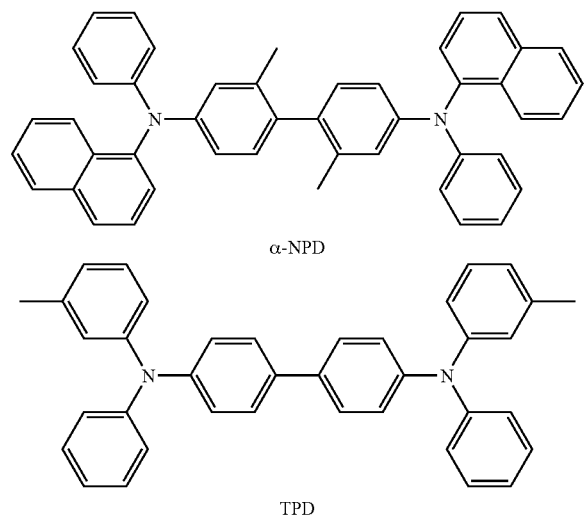

α-NPD

TPD

The thickness of the HTL may be in a range of about 50 to about 1000 Å, and for example, in a range of about 100 to about 600 Å. When the thickness of the HTL is less than 50 Å, a hole transporting ability of the HTL may be reduced. On the other hand, when the thickness of the HTL is greater than about 1000 Å, the driving voltage of the device may be increased.

Then, an EML may be formed on the HTL by spin coating, casting, LB, or the like. When the EML is formed by spin coating, the conditions for coating are similar to those for the formation of the HIL, although the conditions for coating may vary according to the material that is used to form the EML.

The EML includes the polymer of Formula 7 and may further include a host material as described above.

The thickness of the EML may be in a range of about 100 to about 1000 Å, for example, in a range of about 200 to about 600 Å. When the thickness of the EML is less than about 100 Å, the emissive ability of the EML may be reduced. On the other hand, when the thickness of the EML is greater than about 1000 Å, the driving voltage of the device may be increased.

Even though not shown in FIG. 1, at least one layer of a hole blocking layer ("HBL"), an electron transport layer ("ETL"), and an electron injection layer ("EIL") may further be formed between the EML and the second electrode.

The HBL may inhibit diffusion of triplet excitons or holes from the EML to the second electrode. The HBL may be formed using vacuum deposition, spin coating, casting, LB, or the like. When the HBL is formed by vacuum deposition or spin coating, the conditions for deposition and coating are similar to those for the formation of the HIL, although the conditions for deposition and coating may vary according to the material that is used to form the HBL. The HBL may be formed of a known material, for example, an oxadiazole derivative, a triazole derivative, a phenanthroline derivative, or BCP.

The thickness of the HBL may be in a range of about 50 to about 1000 Angstroms ("Å"), and for example, in a range of about 100 to about 300 Å. When the thickness of the HBL is less than 50 Å, the hole blocking ability of the HBL may be reduced. On the other hand, when the thickness of the HBL is greater than about 1000 Å, the driving voltage of the device may be increased.

Then, an ETL may be formed on the HBL or EML by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL. The ETL may be formed of a quinoline derivative which stably transports injected electrons from a cathode, in particular, a quinoline derivative, 4,7-diphenyl-1,10-phenanthroline (Bphen), or the like.

The thickness of the ETL may be in a range of about 100 to about 1000 Å, for example, in a range of about 200 to about 500 Å. When the thickness of the ETL is less than about 100 Å, the electron transporting ability of the ETL may be reduced. On the other hand, when the thickness of the ETL is greater than about 1000 Å, the driving voltage of the device may be increased.

Then, an EIL, which is formed of a material allowing easy injection of electrons from a cathode, may be formed on the ETL. The material that is used to form the EIL is not limited.

The EIL may be formed of a known material such as LiF, NaCl, CsF, $Li_2O$, and BaO. Conditions for the deposition of the EIL are, in general, similar to conditions for the formation of the HIL, although they may vary according to the material that is used to form the EIL.

The thickness of the EIL may be in a range of about 1 to about 100 Å, for example, in a range of about 5 to about 50 Å. When the thickness of the EIL is less than about 1 Å, the electron injecting ability of the EIL may be reduced. On the other hand, when the thickness of the EIL is greater than about 100 Å, the driving voltage of the device may be increased.

Finally, a second electrode may be formed on the EIL by vacuum deposition, sputtering, or the like. The second electrode may be used as a cathode. The second electrode may be formed of a low work-function metal, alloy, electrically conductive compound, or a combination of these. In particular, the second electrode may be formed of Ba, Li, Mg, Al, Al—Li, Ca, Mg—In, Mg—Ag, or the like. The second electrode may be formed of a multilayer having at least two layers using at least two materials. Alternatively, a transparent cathode formed of ITO or IZO may be used to produce a front surface light emitting device.

This disclosure is further exemplified by the following Examples, which are non-limiting.

EXAMPLES

Synthesis Example 1

Synthesis of Compound 1

Compound 1 is synthesized through Reaction Scheme 1 below:

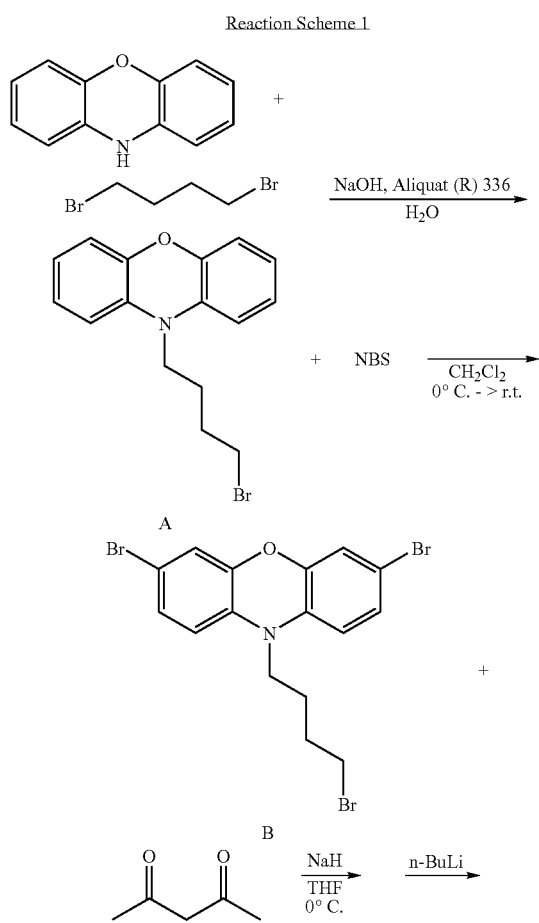

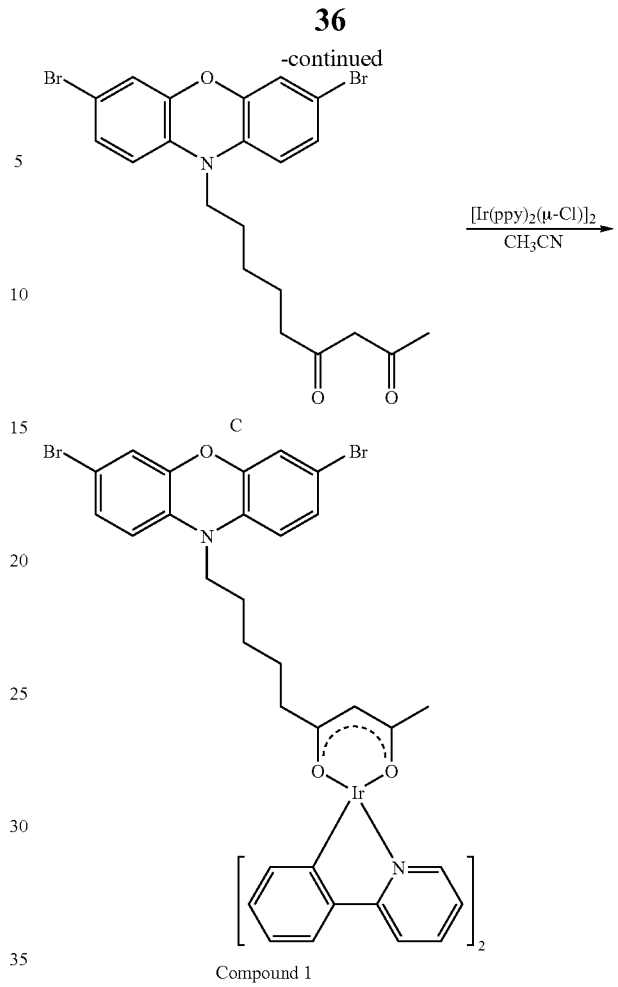

Synthesis of Compound A 2.43 g (12.9 mmoL) of phenoxazine, 31 mL (257 mmoL) of 1,4-dibromobutane, 14.4 g (360 mmoL) of NaOH, two drops of Aliquat® 336, and 44 mL of water are mixed, and the mixture is boiled in an oil bath. When the reaction is terminated, an organic layer is subjected to extraction with methyl chloride (MC) and dried over $MgSO_4$. Then, the solvent is removed in a rotary, and residual 1,4-dibromobutane is removed by distillation using Kugel Rohr in a vacuum. Then, the resultant is subjected to column chromatography to obtain Compound A (yield: 98%).

$^1$H-NMR (300 MHz, $CDCl_3$) δ (ppm) 6.87-6.81 (m, 2H), 6.72-6.66 (t, 4H), 6.53-6.50 (d, 2H), 3.57-3.47 (m, 4H), 2.04-1.98 (m, 2H), 1.91-1.84 (m, 2H).

$^{13}$C-NMR (75 MHz, $CDCl_3$) δ (ppm) 162.33, 145.04, 133.20, 123.72, 120.97, 115.50, 111.32, 43.13, 33.07, 29.99, 23.78.

Synthesis of Compound B 2.23 g (7.01 mmoL) of Compound A is dissolved in 100 mL of MC, and 3.2 g (17.5 mmoL) of NBS is drop by drop added thereto at 0° C. Then, the mixture is heated to room temperature. When the reaction is terminated, the resultant is subjected to a work-up procedure and column chromatography to obtain Compound B (yield: 76%).

$^1$H-NMR (300 MHz, $CDCl_3$) δ (ppm) 6.88-6.84 (dd, 2H), 6.72-6.69 (d, 2H), 6.28-6.25 (d, 2H), 3.45-3.37 (m, 2H), 1.96-1.91 (m, 2H), 1.79-1.71 (m, 2H).

$^{13}$C-NMR (75 MHz, $CDCl_3$) δ (ppm) 145.06, 131.81, 126.52, 118.61, 112.39, 112.32, 43.22, 32.76, 30.27, 29.60, 23.32.

Synthesis of Compound C 1.2 mL (11.4 mmoL) of acetylacetone is added to a reaction flask including 720 mg (28.5 mmoL) of NaH and 60 mL of THF at 0° C., and the mixture is stirred for 10 minutes. Then, 14.4 mL (22.7 mmoL) of n-BuLi (1.6 M in Hexane) is added thereto, and the mixture is stirred for 30 minutes. The dianion synthesized as described above is added drop by drop to a flask including 1.81 g (3.80 mmoL) of Compound B dissolved in 60 mL of THF. When the reaction is terminated, HCl (aq.) is added thereto, and the resultant is subjected to a work-up procedure and column chromatography to obtain Compound C (yield: 52%).

$^1$H-NMR (300 MHz, CDCl$_3$) δ (ppm) 6.89-6.85 (dd, 2H), 6.70 (d, 2H), 6.27-6.25 (d, 2H), 5.49 (s, 1H), 3.40-3.34 (m, 2H), 2.32-2.24 (m, 2H), 3.06 (s, 3H), 1.70-1.60 (m, 4H), 1.43-1.41 (m, 2H).

$^{13}$C-NMR (75 MHz, CDCl$_3$) δ (ppm) 193.87, 191.16, 145.13, 132.03, 126.54, 118.57, 112.40, 112.25, 99.93, 43.97, 38.07, 26.35, 25.25, 24.88, 24.64, 24.53.

Synthesis of Compound 1

127 mg (0.257 mmoL) of Compound C, 138 mg (0.128 mmoL) of [Ir(ppy)$_2$(μ-Cl)]$_2$, 54 mg (0.514 mmoL) of Na$_2$CO$_3$, 15 mL of CH$_3$CN are mixed, and the mixture is boiled for 24 hours to form a complex. Thus, Compound 1 is synthesized (65%).

$^1$H-NMR (300 MHz, CDCl$_3$) δ (ppm) 8.55-8.50 (t, 2H), 7.88-7.66 (m, 4H), 7.58-7.49 (dd, 2H), 7.14-7.10 (t, 2H), 6.87-6.67 (m, 8H), 6.34-6.27 (m, 2H), 6.15-6.12 (d, 2H), 5.22 (s, 1H), 3.11-3.06 (m, 2H), 2.08-2.02 (m, 2H), 2.82 (s, 3H), 1.43-1.26 (m, 4H), 1.14-1.02 (m, 2H).

Synthesis Example 2

Synthesis of Compound 2

Compound 2 is synthesized through Reaction Scheme 2 below:

Reaction Scheme 2

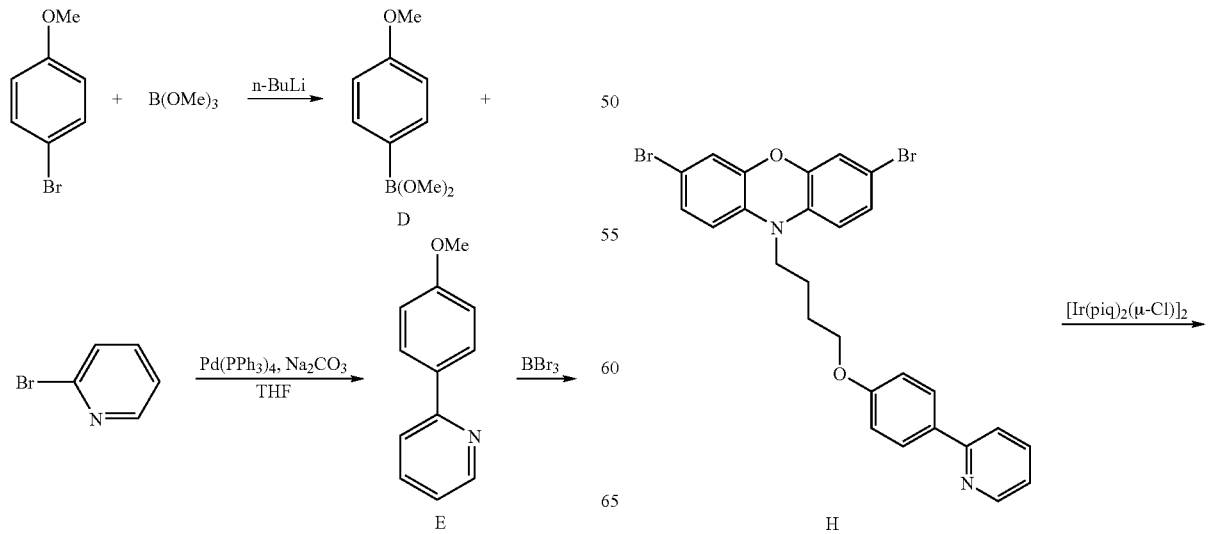

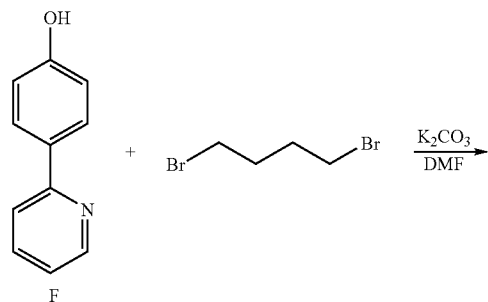

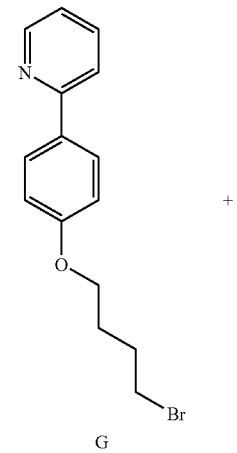

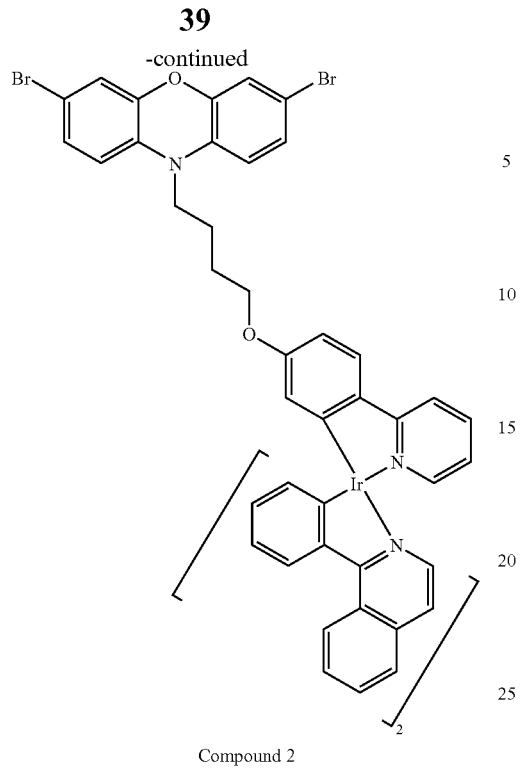

Compound 2

Synthesis of Compound D 28.9 g (155 mmoL) of 4-bromoanisole is mixed with n-BuLi and trimethylborate at −78° C., and the mixture is treated with an acid to obtain an aqueous layer. The aqueous layer is subjected to extraction with MC and column chromatography to obtain Compound D (yield: 60%).

Synthesis of Compound E 14.1 g (92.7 mmoL) of Compound D, THF, $Na_2CO_3$, 5.4 g (4.7 mmoL) of $Pd(PPh_3)_4$, 14.7 g (93.3 mmoL) of 2-bromopyridine are mixed to obtain an aqueous layer. The aqueous layer is subjected to extraction with MC, and an organic layer is subjected to an anhydrous treatment to obtain Compound E (yield: 70%).

Synthesis of Compound G 65.3 g of $BBr_3$ is added to 12.1 g (65.3 mmoL) of Compound E at −10□, and the mixture is stirred at room temperature for 2 hours. Water is added to the resultant mixture to form an aqueous layer. The aqueous layer is subjected to extraction to obtain Compound F. Then, 7.8 g (46 mmoL) of Compound F is mixed with 14.8 g of 1,4-dibromobutane in DMF in the presence of $K_2CO_3$ at 80° C. for 2 hours. The resultant is filtered, concentrated, and subjected to column chromatography to obtain Compound G (yield: 40%).

Synthesis of Compound H 10.4 g (18.4 mmoL) of Compound G is mixed with 6.85 g (20.1 mmoL) of 2,6-dibromophenoxazine to obtain Compound H (yield: 30%).
$^1$H-NMR (300 MHz, $CDCl_3$) δ (ppm) 8.69 (d, 1H), 7.99-7.96 (d, 2H), 7.78-7.69 (m, 2H), 7.23-7.19 (t, 1H), 7.03-7.00 (d, 2H), 6.92-6.88 (dd, 2H), 6.77 (d, 2H), 6.39-6.32 (d, 2H), 4.16 (t, 2H), 3.63 (t, 2H), 1.96-1.76 (m, 4H).

Synthesis of Compound 2

113 mg (0.20 mmoL) of Compound H, 127 mg (0.10 mmoL) of $[Ir(piq)_2(\mu-Cl)]_2$, and 35 mg (0.127 mmoL) of $AgCF_3SO_3$ are dissolved in 3 mL of ethoxyethanol, and the mixture is subjected to nitrogen flushing and boiled in an oil bath for 24 hours. When the reaction is terminated, the resultant is cooled to room temperature, and the solvent is removed. Then, the resultant is subjected to column chromatography to obtain Compound 2 (yield: 30%).
$^1$H-NMR (300 MHz, $CDCl_3$) δ (ppm) 8.56-8.40 (m, 3H), 8.12 (d, 2H), 7.98 (d, 3H), 7.7 (d, 2H), 7.54-7.50 (m, 6H), 7.32-7.28 (m, 6H), 7.1 (d, 2H), 7.93-6.87 (m, 7H), 6.23 (d, 2H), 3.93 (t, 4H), 1.71-1.52 (m, 4H).

Synthesis Example 3

Synthesis of Compound 3

Compound 3 is synthesized through Reaction Scheme 3 below:

Reaction Scheme 3

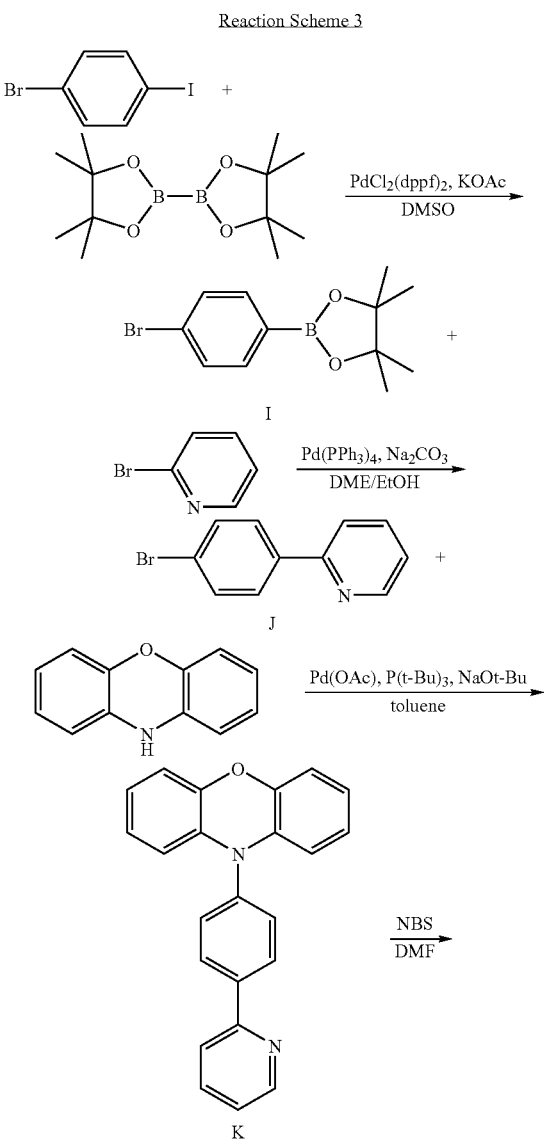

-continued

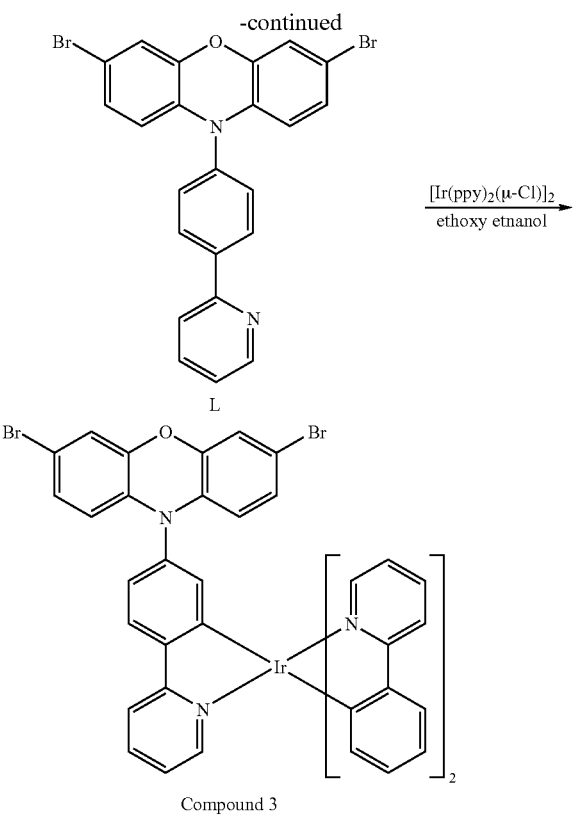

Compound 3

Synthesis of Compound I 245 mg (0.30 mmoL) of PdCl$_2$(dppf)$_2$ and 3 g (30 mmoL) of KOAC are added to a flask, and the mixture is subjected to nitrogen flushing. Air in the flask is removed, and 2.9 g (10 mmoL) of 1-bromo-4-iodobenzene and 60 mL of DMSO are added to the flask. The flask is placed in an oil bath and heated to 100° C. After the reaction is terminated, the resultant is subjected to extraction with MC and washed with H$_2$O. The resultant is subjected to column chromatography to obtain Compound I (yield: 78%).

Synthesis of Compound J 522 microliters ("μl") (5.30 mmoL) of 2-bronopyridine and 18 mg (0.159 mmoL) of Pd(PPh$_3$)$_4$ are dissolved in 15 mL of DME, and the mixture is subjected to nitrogen flushing. 1.5 g (5.3 mmoL) of Compound I and 15 mL of ethanol (EtOH) are added to the mixture, and Na$_2$CO$_3$ (2.0M in H$_2$O, 8.0 mL) is added thereto. The mixture is bubbled with N$_{2(g)}$ for 20 minutes and heated. When the reaction is terminated, the resultant is subjected to a work-up procedure and column chromatography to obtain Compound J (yield: 78%).

Synthesis of Compound K 967 mg (4.10 mmoL) of Compound J, 759 mg (4.14 mmoL) of phenoxazine, 28 mg (0.123 mmoL) of Pd(OAc)$_2$, 99 mg (0.492 mmoL) of P(t-Bu)$_3$, and 569 mg (5.92 mmoL) of NaOt-Bu are dissolved in 40 mL of toluene, and the mixture is heated to 110° C., and the temperature is maintained until the reaction is terminated. When the reaction is terminated, the resultant is subjected to a work-up procedure and column chromatography to obtain Compound K (yield: 80%).

$^1$H-NMR (300 MHz, CDCl$_3$) δ (ppm) 8.78-8.75 (m, 1H), 8.27-8.24 (d, 2H), 7.81-7.79 (m, 2H), 7.48-7.45 (d, 2H), 7.32-7.27 (m, 1H), 6.77-6.60 (m, 7H), 6.07-6.04 (dd, 2H).

$^{13}$C-NMR (75 MHz, CDCl$_3$) δ (ppm) 156.41, 149.88, 143.99, 139.65, 139.60, 137.02, 134.28, 131.16, 129.66, 123.35, 122.77, 122.60, 121.47, 120.72, 115.84, 115.53, 113.40.

Synthesis of Compound L 772 mg (2.29 mmoL) of Compound K is dissolved in 20 mL of DMF 20 mL, and the mixture is cooled to 0° C. 823 mg (4.58 mmoL) of NBS is added thereto, and the reaction is conducted at room temperature. When the reaction is terminated, the resultant is subjected to a work-up procedure and column chromatography to obtain Compound L (yield: 79%).

$^1$H-NMR (300 MHz, CDCl$_3$) δ (ppm) 8.75-8.73 (dd, 1H), 8.25-8.20 (d, 2H), 7.83-7.80 (m, 2H), 7.42-7.38 (d, 2H), 7.33-7.28 (m, 1H), 6.83 (d, 2H), 6.73-6.70 (dd, 2H), 5.88-5.85 (d, 2H).

$^{13}$C-NMR (75 MHz, CDCl$_3$) δ (ppm) 156.09, 149.86, 144.04, 140.04, 138.60, 136.95, 133.02, 130.61, 129.81, 126.23, 122.65, 120.65, 118.61, 114.41, 112.90.

Synthesis of Compound 3

108.7 mg (0.22 mmoL) of Compound L, 118 mg (0.11 mmoL) of [Ir(ppy)$_2$(μ-Cl)]$_2$, and 38 mg (0.148 mmoL) of AgCF$_3$SO$_3$ are dissolved in 3 mL of ethoxyethanol, and the mixture is subjected to nitrogen flushing and boiled in an oil bath for 24 hours. When the reaction is terminated, the resultant is cooled to room temperature and subjected to column chromatography to obtain Compound 3 (yield: 27%).

$^1$H-NMR (300 MHz, CDCl$_3$) δ (ppm) 8.56 (d, 3H), 8.0-7.9 (d, 2H), 7.54-7.47 (m, 6H), 7.40-7.37 (m, 6H), 6.98-6.90 (m, 7H), 6.6 (t, 2H), 6.31 (d, 2H).

Synthesis Example 4

Synthesis of Polymer 1

Synthesis of Polymer A 240 mg of Ni(cod)$_2$, 134 mg of 2,2-bipyridyl, and 106 μl of 1,5-cyclooctadiene are dissolved in 20 mL of THF, and the mixture is subjected to nitrogen flushing and heated for 30 minutes to obtain an activation catalyst complex. 540 mg (0.5 mmoL) of 2,7-dibromo-(2',3',6',7'-tetraoctyloxy)spirofluorene, 293 mg (0.4 mmoL) of 2,7-dibromo-9,9-dioctyloxyphenylfluorene, and 56 mg (0.1 mmoL) of Compound H are dissolved in 10 mL of THF, and the mixture is added to the activation catalyst complex. Then, the resulting mixture is reacted at 60° C. for 3 days. When the reaction is terminated, the resultant is subjected to reprecipitation in toluene to obtain Polymer A. Impurities are removed from Polymer A using a Soxhlet device, and the resultant is dried in a vacuum oven for 24 hours.

$^1$H-NMR (300 MHz, CDCl$_3$) δ (ppm) 7.87-7.82 (t, 1H), 7.79-7.62 (d, 1H), 7.51-7.48 (br, 2H), 7.35-7.28 (m, 2H), 7.25-7.18 (d, 2H), 7.13-7.10 (br, 2H), 6.73-6.23 (d, 2H), 6.23-6.19 (br, 1H), 4.13 (t, 2H), 3.89-3.85 (t, 2H), 3.70 (br, 2H), 1.91 (m, 2H), 1.86-1.71 (m, 2H), 1.70-1.63 (m, 6H), 1.31-1.21 (m, 30H), 0.90-0.89 (m, 9H).

GPC analysis: Mn=7929, PDI=2.33.

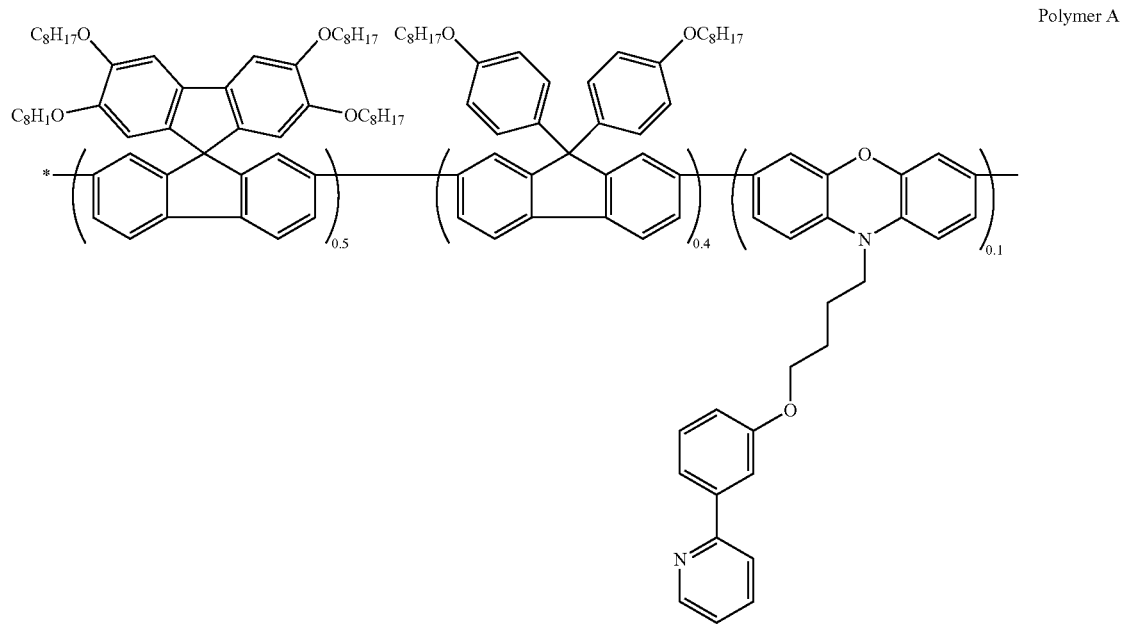

Polymer A

Synthesis of Polymer 1

200 mg of Polymer A is dissolved in 30 mL of toluene in a 250 mL-2-neck flask having a thermometer, a mechanical stirrer, and a reflux condenser in a nitrogen atmosphere, and 19 mg of $AgCF_3SO_3$ is added thereto. 30 mL of 2-methoxyethanol slurry including 50 mg of $[Ir(piq)_2(\mu\text{-}Cl)]_2$ is added to the mixture, and the resultant is stirred at 110° C. for 24 hours. When the reaction is terminated, the resultant is cooled to room temperature, and the solvent is removed by distillation under a reduced pressure. A process of dissolving the resultant in toluene and precipitating the resultant in methanol is repeated twice to obtain 160 mg of Polymer 1.

$^1$H-NMR (300 MHz, $CDCl_3$) δ 7.65-7.62 (m, 1H), 7.57-7.51 (d, 1H), 7.48 (br, 2H), 7.28 (d, 1H), 7.23 (d, 1H), 7.18-7.13 (d, 2H), 7.06-6.85 (m, 2H), 6.78-6.73 (d, 2H), 6.37 (br, 1H), 4.14 (t, 2H), 3.89-3.85 (t, 2H), 3.70 (t, 2H), 1.91 (m, 2H), 1.74 (m, 2H), 1.73-1.54 (m, 6H), 1.32-1.21 (m, 29H), 0.97 (m, 9H).

GPC analysis: Mn=8565, PDI=1.88.

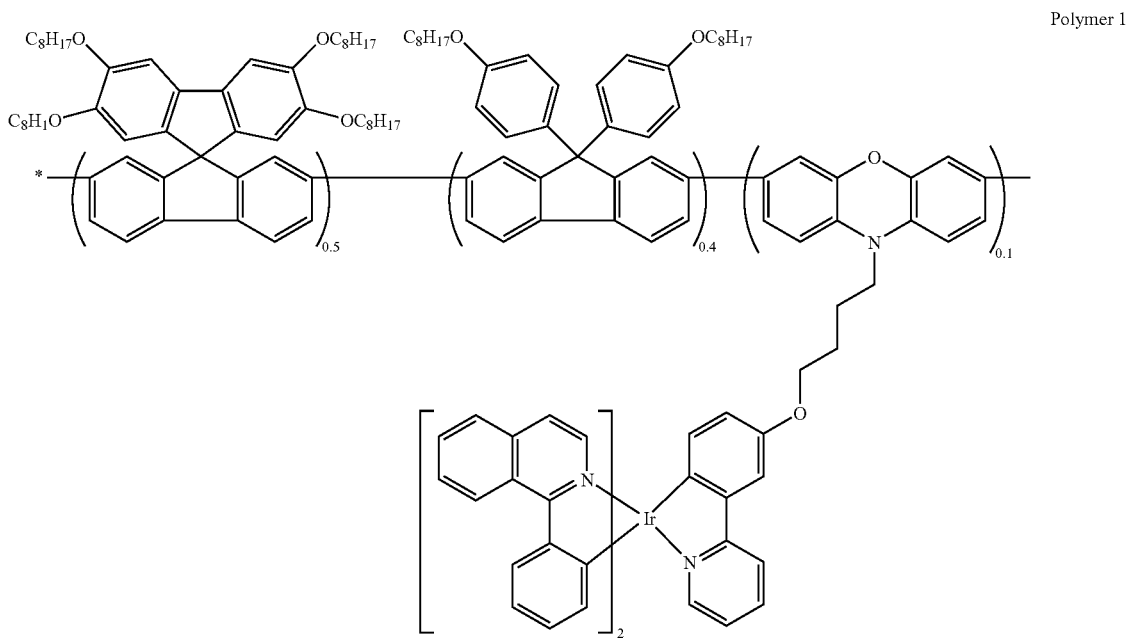

Polymer 1

Synthesis Example 5

Synthesis of Polymer 2

Yamamoto Polymerization:

240 mg of Ni(cod)$_2$, 134 mg of 2,2-bipyridyl, and 106 microliters of 1,5-cyclooctadiene are dissolved in 20 mL of THF, and the mixture is subjected to nitrogen flushing and heated for 30 minutes to obtain an activation catalyst complex. 278 mg (0.28 mmoL) of 2,7-dibromo-(2',3',6',7'-tetraoctyloxy)spirofluorene, 167 mg (0.224 mmoL) of 2,7-dibromo-9,9-dioctyloxyphenylfluorene, and 55 mg (0.05 mmoL) of Compound 1 are dissolved in 10 mL of THF, and the mixture is added to the activation catalyst complex. Then, the resulting mixture is reacted at 60° C. for 3 days. When the reaction is terminated, the resultant is subjected to reprecipitation in toluene to obtain Polymer 2. Impurities are removed from Polymer 2 using a Soxhlet device, and the resultant is dried in a vacuum oven for 24 hours.

$^1$H-NMR (300 MHz, CDCl$_3$) δ 7.72 (m, 2H), 7.57 (br, 2H), 7.41 (m, 3H), 7.24-7.19 (m, 3H), 7.27 (d, 2H), 6.79 (m, 3H), 4.06 (t, 4H), 3.94 (br, 7H), 1.74-1.71 (m, 10H), 1.03 (m, 48H), 0.86 (t, 18H).

Synthesis Example 5

Synthesis of Polymer 3

240 mg of Ni(cod)$_2$, 134 mg of 2,2-bipyridyl, and 106 µl of 1,5-cyclooctadiene are dissolved in 20 mL of THF, and the mixture is subjected to nitrogen flushing and heated for 30 minutes to obtain an activation catalyst complex. 278 mg (0.28 mmoL) of 2,7-dibromo-(2',3',6',7'-tetraoctyloxy) spirofluorene, 84 mg (0.112 mmoL) of 2,7-dibromo-9,9-dioctyloxyphenylfluorene, 66 mg (0.112 mmoL) of 3,7-dibromo-10-(4'-heptylbiphenyl-4-yl)-10H-phenoxazine, and 55 mg (0.05 mmoL) of Compound 1 are dissolved in 10 mL of THF, and the mixture is added to the activation catalyst complex. Then, the resulting mixture is reacted at 60° C. for 3 days. When the reaction is terminated, the resultant is subjected to reprecipitation in toluene to obtain Polymer 3. Impurities are removed from Polymer 3 using a Soxhlet device, and the resultant is dried in a vacuum oven for 24 hours.

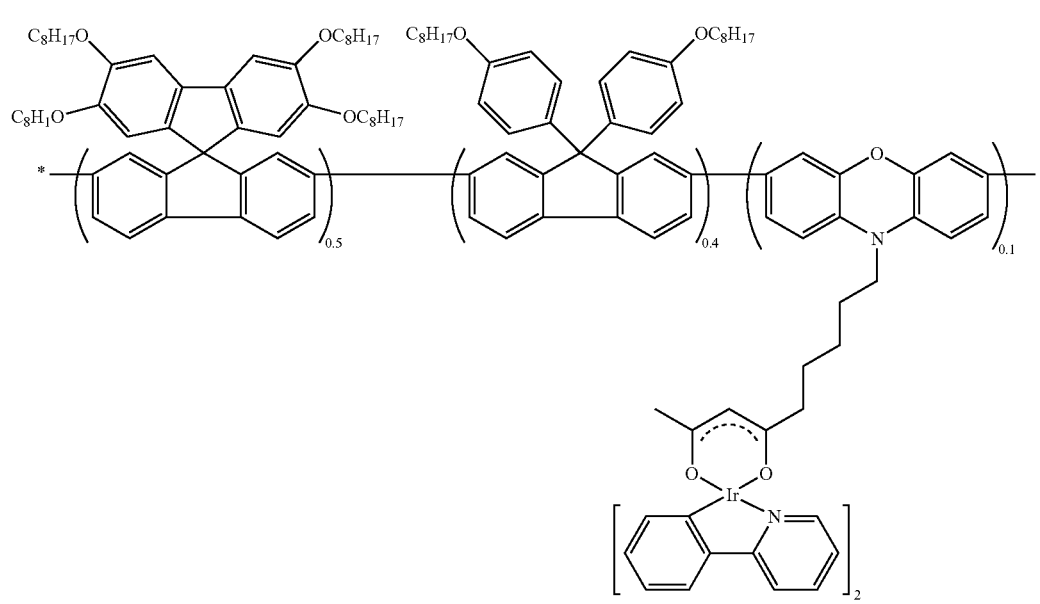

Polymer 2

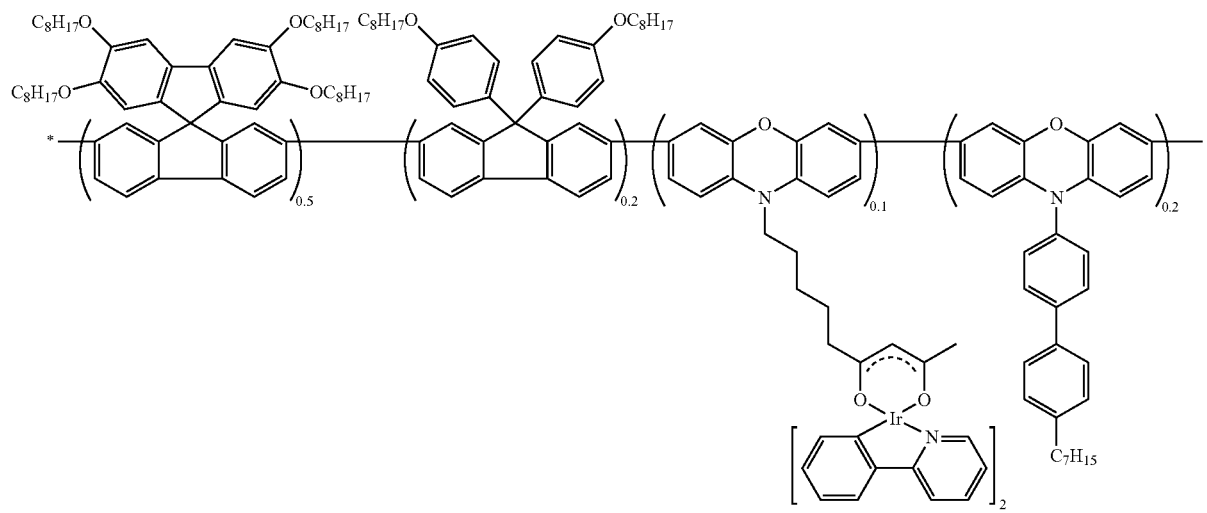

Polymer 3

Example 1

A transparent electrode substrate prepared by coating a glass substrate with an indium-tin oxide (ITO) is washed, and the ITO is patterned using a photosensitive resin and an etchant, and the substrate is washed. PEDOT (Bayer, Batron P 4083) is coated on the ITO to a thickness of about 800 Å, and the resultant is baked at 180° C. for about 1 hour to form a HIL. An EML composition including 99 parts by weight of toluene and 1 part by weight of Polymer 1 is spin-coated on the HIL, and the resultant is baked. The solvent is completely removed in a vacuum oven to form an EML. In this regard, the EML composition is filtered using a 0.2 mm filter before the spin coating. The thickness of the EML is about 80 nm, which is obtained by controlling the concentration of the EML composition and spin coating speed.

Then, Ba and Al are sequentially deposited on the EML using a vacuum evaporator while maintaining $4 \times 10^{-6}$ torr to form a second electrode. The thickness of the layer and the layer growing speed are controlled using a crystal sensor.

Evaluation Example 1

Figure 2:
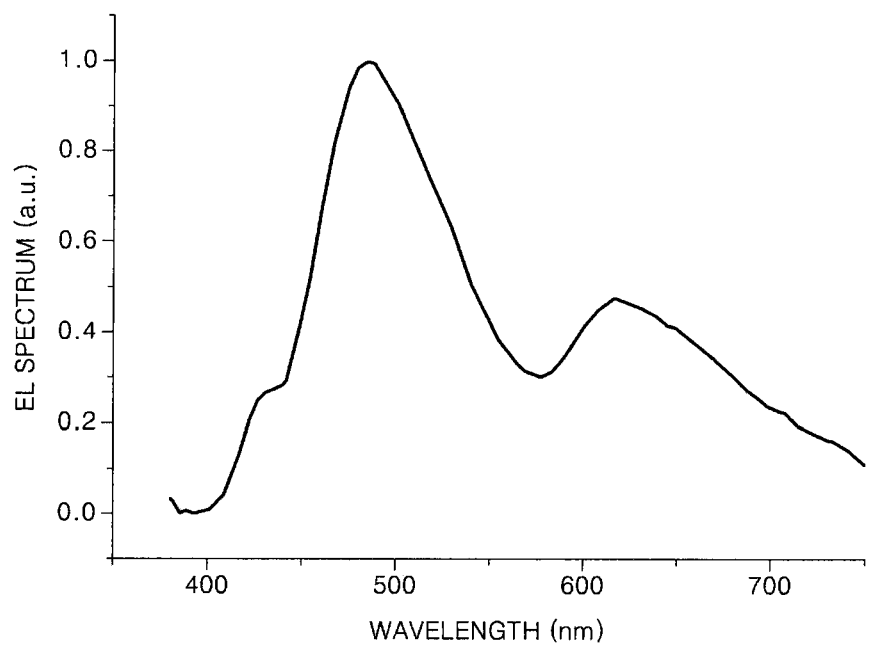
FIG. 2 is a graph of color purity of an OLED according to an exemplary embodiment.
Figure 3:
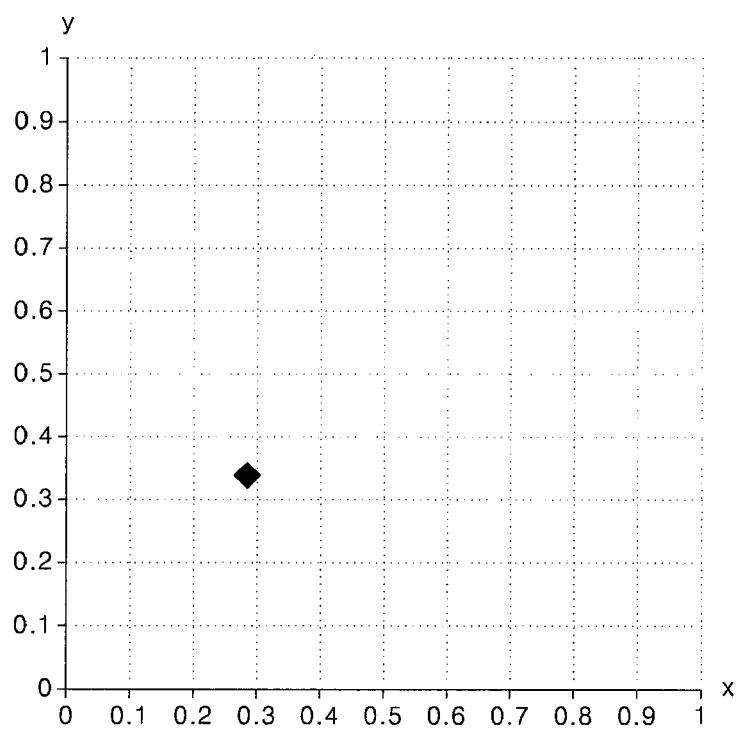
FIG. 3 is a graph of CIE color coordination of an OLED according to an exemplary embodiment.
Figure 4:
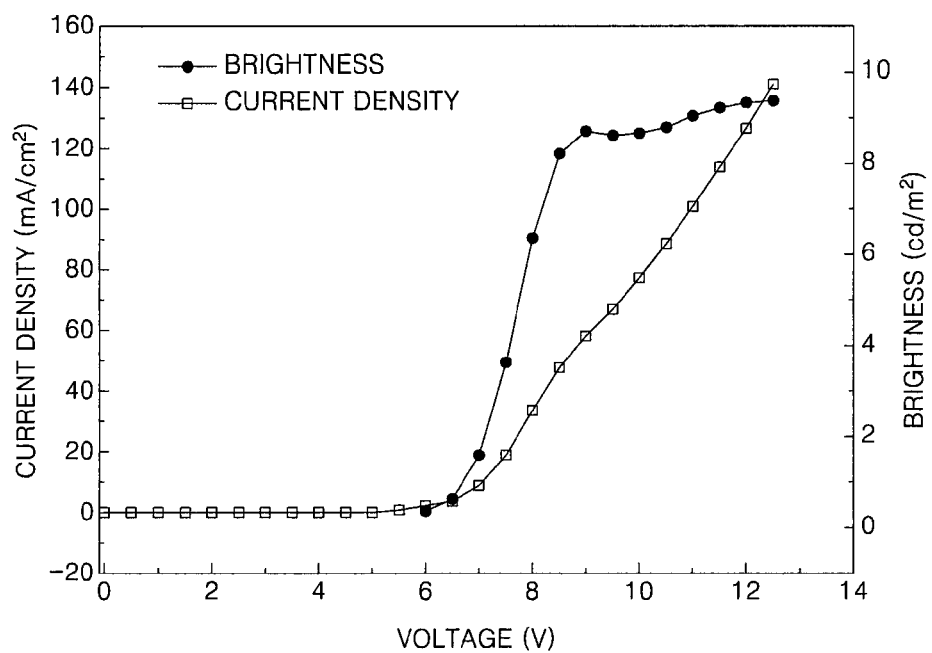
FIG. 4 is a graph of current density-voltage-brightness of an OLED according to an exemplary embodiment.

Color purity of the OLED manufactured according to Example 1 is evaluated using PR650 (Spectroscan) Source Measurement Unit. As a result, the OLED manufactured according to Example 1 emits white light. FIGS. 2, 3, and 4 are graphs of color purity, CIE color coordination, and current density-voltage-brightness.

Because the emitting polymer can emit both fluorescent and phosphorescent lights, a high quality OLED may be manufactured using the emitting polymer.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. The polymer represented by one of Formulae 7a to 7d:

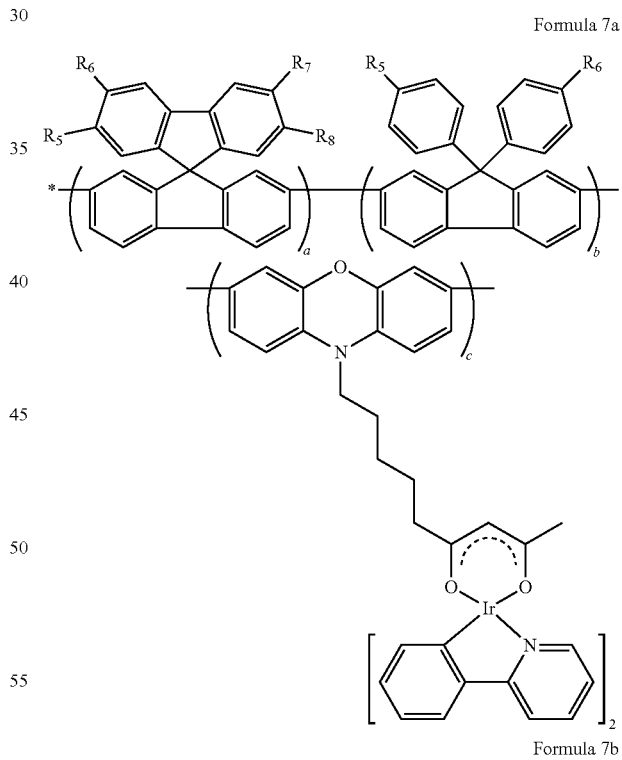

Formula 7a

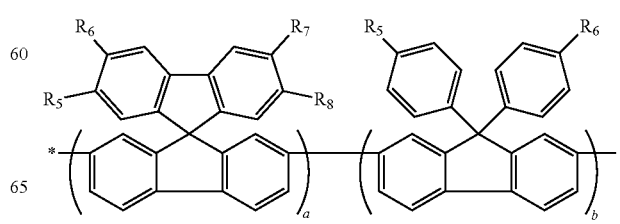

Formula 7b

-continued

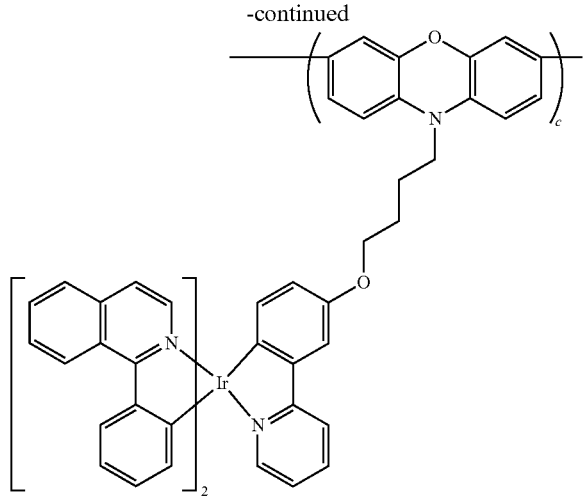

Formula 7c

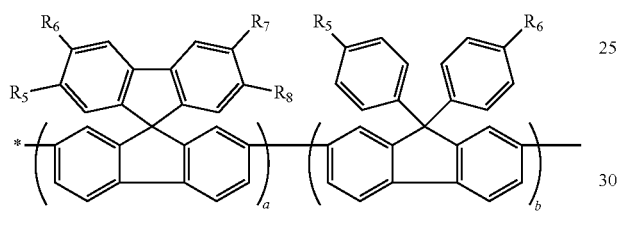

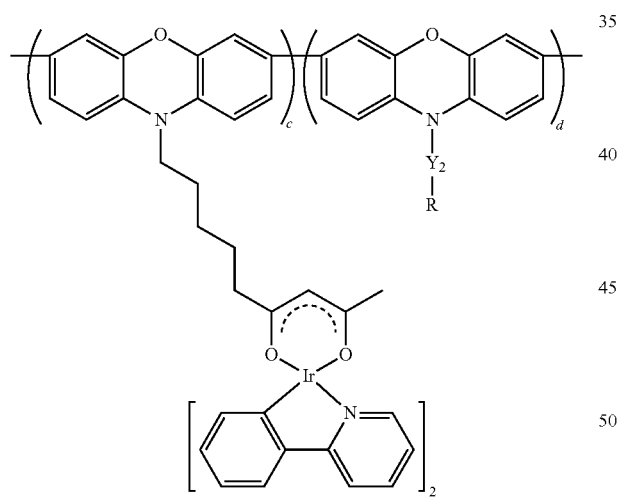

Formula 7d

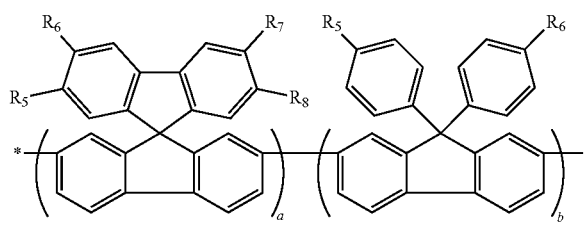

-continued

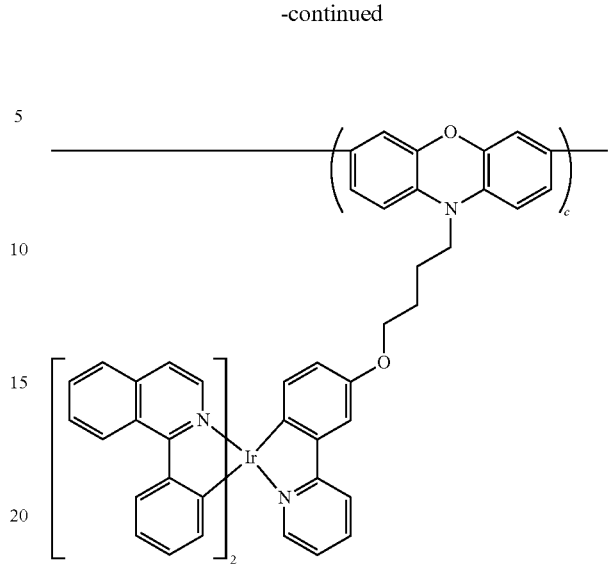

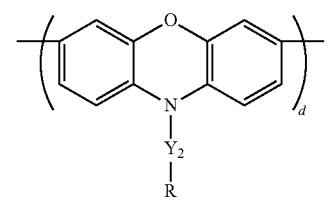

wherein $Y_2$ is a substituted or unsubstituted $C_6$-$C_{30}$ arylene group or a substituted or unsubstituted $C_4$-$C_{30}$ heteroarylene group;

R is selected from the group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_3$-$C_{30}$ cycloalkyl group, a substituted or unsubstituted $C_6$-$C_{30}$ aryl group, and a substituted or unsubstituted $C_6$-$C_{30}$ hetero aryl group;

$R_5$ to $R_8$ are each independently a hydrogen atom, a $C_1$-$C_{20}$ alkyl group, a $C_1$-$C_{20}$ alkoxy group, or a $C_6$-$C_{30}$ aryl group, and a is a real number of $0<a\leq0.99$, b is a real number of $0<b\leq0.99$, c is a real number of $0<c\leq0.99$, and d is a real number of $0\leq d\leq0.99$, wherein a+b+c+d=1.

2. The polymer of claim 1, wherein in Formulae 7c and 7d, d is 0.

3. The polymer of claim 1, wherein the polymer emits one of red light or green light, or both of red and green lights in a repeating group represented by one of the formulae:

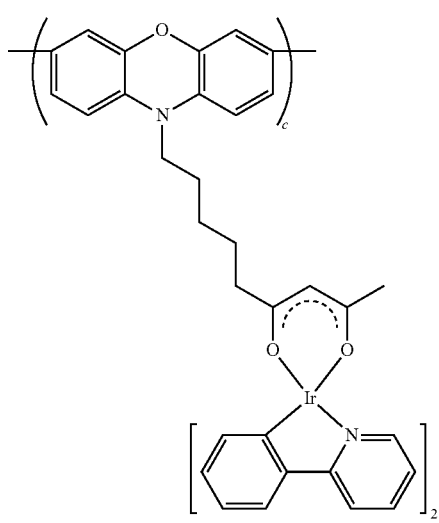
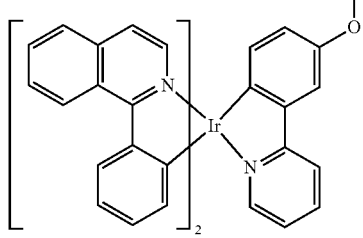
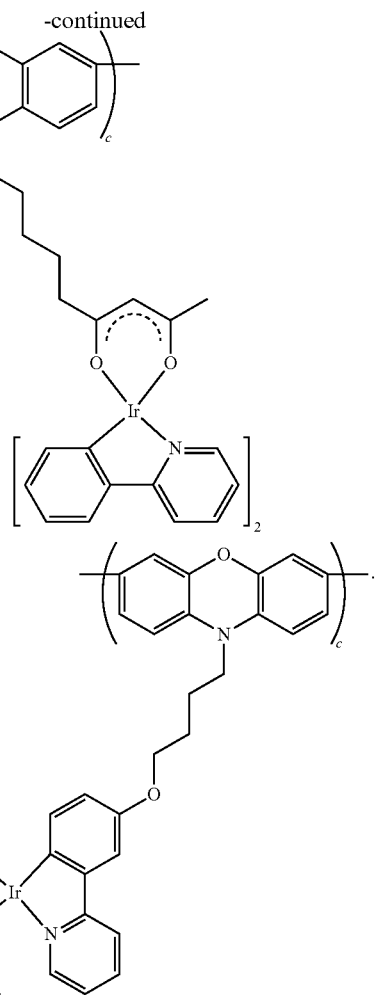
4. The polymer of claim 1, wherein the polymer emits white light.
5. The polymer of claim 1, wherein the polymer has a weight average molecular weight of about 10,000 to about 500,000.
6. An organic light emitting device (OLED) comprising a pair of electrodes and an organic layer comprising a polymer according to claim 1 between the pair of electrodes.
* * * * *